(12) United States Patent
Ariyoshi et al.

(10) Patent No.: US 11,754,580 B2
(45) Date of Patent: Sep. 12, 2023

(54) SAMPLE MEASUREMENT METHOD AND SAMPLE MEASUREMENT DEVICE

(71) Applicant: SYSMEX CORPORATION, Kobe (JP)

(72) Inventors: Shunsuke Ariyoshi, Kobe (JP); Tsuyoshi Fukuzaki, Kobe (JP); Masaki Shiba, Kobe (JP)

(73) Assignee: SYSMEX CORPORATION, Kobe (JP)

( * ) Notice: Subject to any disclaimer, the term of this patent is extended or adjusted under 35 U.S.C. 154(b) by 1140 days.

(21) Appl. No.: 16/232,290

(22) Filed: Dec. 26, 2018

(65) Prior Publication Data

US 2019/0204349 A1 Jul. 4, 2019

(30) Foreign Application Priority Data

Dec. 28, 2017 (JP) ................................. 2017-253156

(51) Int. Cl.
*G01N 35/10* (2006.01)
*G01N 33/49* (2006.01)
(Continued)

(52) U.S. Cl.
CPC ....... *G01N 35/1009* (2013.01); *G01N 33/491* (2013.01); *G01N 33/4905* (2013.01); *G01N 33/86* (2013.01); *G01N 35/1004* (2013.01); *G01N 35/1011* (2013.01); *G01N 21/76* (2013.01); *G01N 35/1079* (2013.01);
(Continued)

(58) Field of Classification Search
None
See application file for complete search history.

(56) References Cited

U.S. PATENT DOCUMENTS 5,452,619 A 9/1995 Kawanabe et al.
5,972,712 A 10/1999 Baugh et al.
(Continued)

FOREIGN PATENT DOCUMENTS

CN 102348988 A 2/2012
JP H01-227063 A 9/1989
(Continued)

OTHER PUBLICATIONS

The Office Action (JPOA) dated Dec. 7, 2021 in a counterpart Japanese patent application.
(Continued)

*Primary Examiner* — P. Kathryn Wright
(74) *Attorney, Agent, or Firm* — METROLEX IP LAW GROUP, PLLC

(57) ABSTRACT

A sample measurement method of performing first measurement for a blood coagulation test and second measurement for a test different from the blood coagulation test includes: dispensing a sample for use in the first measurement into a first container from a sample container; dispensing the sample for use in the second measurement into a second container different from the first container from the sample container from which the sample for use in the first measurement has been dispensed; performing the first measurement based on the sample dispensed into the first container; and performing the second measurement based on the sample dispensed into the second container.

17 Claims, 17 Drawing Sheets

(51) Int. Cl.
  *G01N 33/86* (2006.01)
  *G01N 21/82* (2006.01)
  *G01N 21/76* (2006.01)
  *G01N 35/00* (2006.01)

(52) U.S. Cl.
  CPC .......... *G01N 2021/825* (2013.01); *G01N 2035/0097* (2013.01); *G01N 2035/00277* (2013.01); *G01N 2035/00495* (2013.01); *G01N 2035/1025* (2013.01)

(56) References Cited

U.S. PATENT DOCUMENTS

| | | | |
|---|---|---|---|
| 2006/0077376 A1* | 4/2006 | Maroney | G01N 35/1009 422/67 |
| 2007/0020764 A1 | 1/2007 | Miller | |
| 2009/0081794 A1* | 3/2009 | Wakamiya | G01N 35/0092 422/68.1 |
| 2012/0003731 A1 | 1/2012 | Kuroda | |

FOREIGN PATENT DOCUMENTS

| | | |
|---|---|---|
| JP | H04-249766 A | 9/1992 |
| JP | H06-82461 A | 3/1994 |
| JP | H06-78866 U | 11/1994 |
| JP | H10-221346 A | 8/1998 |
| JP | 2001-013151 A | 1/2001 |
| JP | 2001-99848 A | 4/2001 |
| JP | 2003-4753 A | 1/2003 |
| JP | 2005-43270 A | 2/2005 |
| JP | 2009-74885 A | 4/2009 |
| JP | 2010-048594 A | 3/2010 |
| JP | 2017-15671 A | 1/2017 |
| WO | WO-2010013033 A1 * | 2/2010 ............ G01N 15/05 |
| WO | 2013187210 A1 | 12/2013 |
| WO | 2016/017289 A1 | 2/2016 |
| WO | 2017/043196 A1 | 3/2017 |
| WO | 2017/159359 A1 | 9/2017 |

OTHER PUBLICATIONS

The extended European search report (EESR) dated Jun. 6, 2019 in a counterpart European patent application.
The Office Action (CNOA) dated Mar. 30, 2022 in a counterpart Chinese patent application.
The Office Action (JPOA) dated Jun. 22, 2021 in a counterpart Japanese patent application.
The Office Action (EPOA) dated Jan. 25, 2022 in a counterpart European patent application.
The Office Action (CNOA) dated Nov. 16, 2022 in a counterpart Chinese patent application.
The Office Action (CNOA) dated Feb. 28, 2023 in a counterpart Chinese patent application.
The Communicaton pursuant to Article 94(3) EPC dated May 24, 2023 in a counterpart European patent application.

* cited by examiner

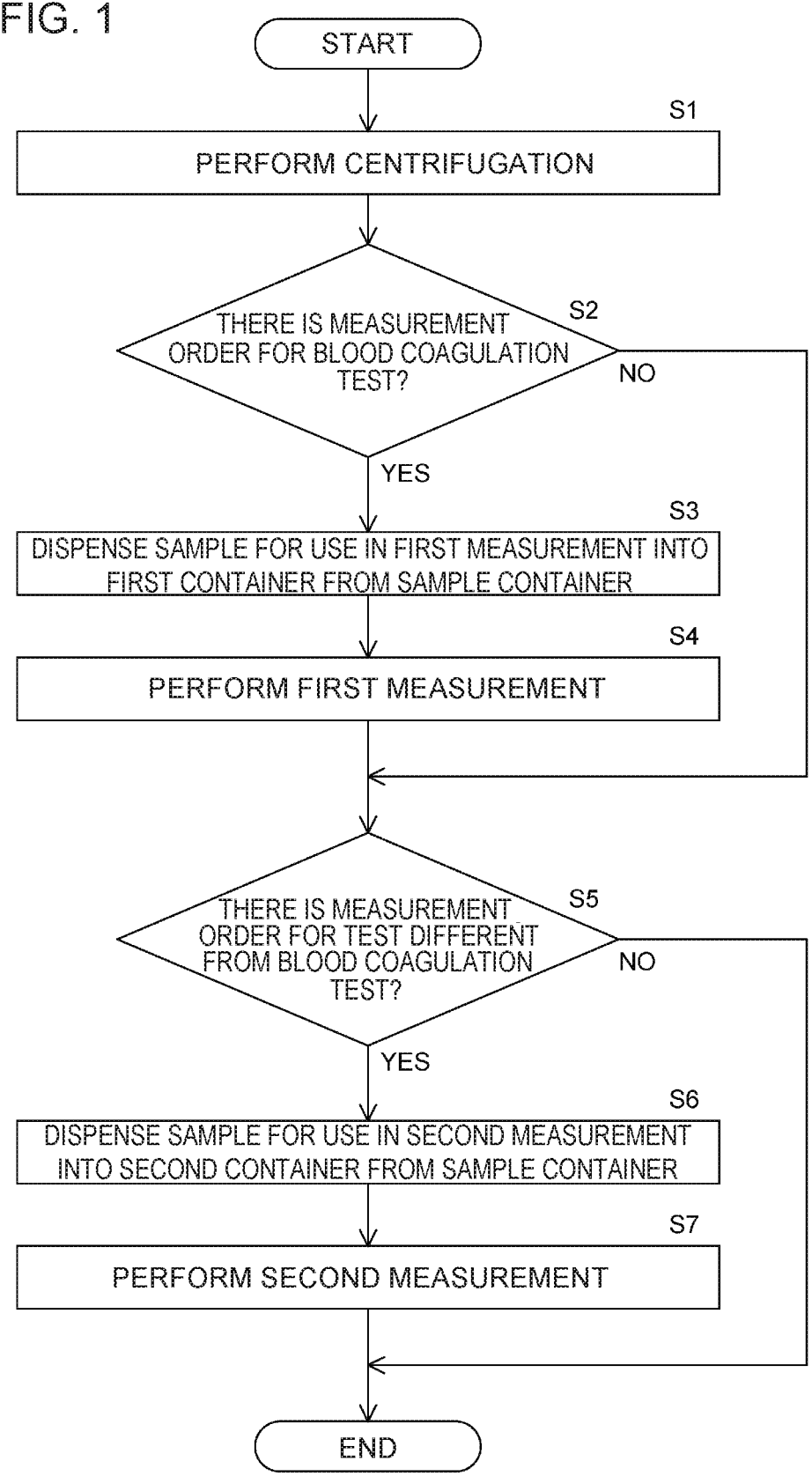

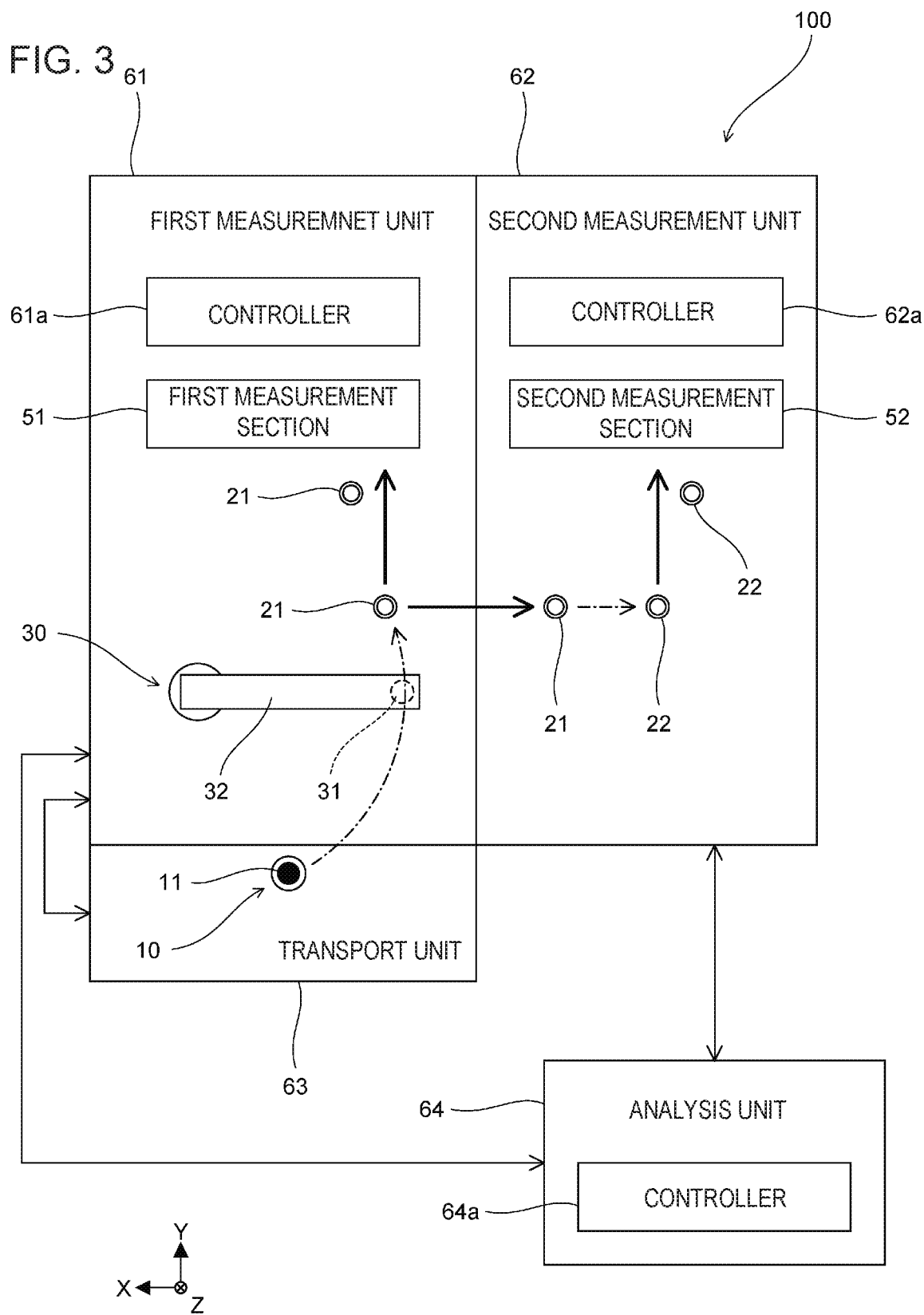

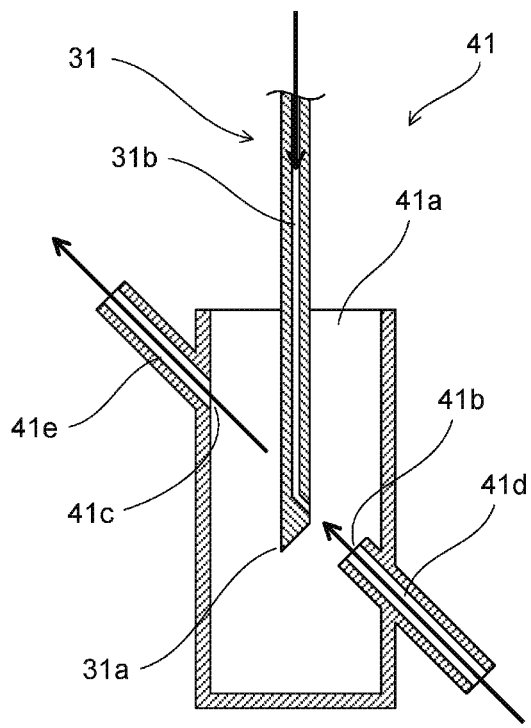
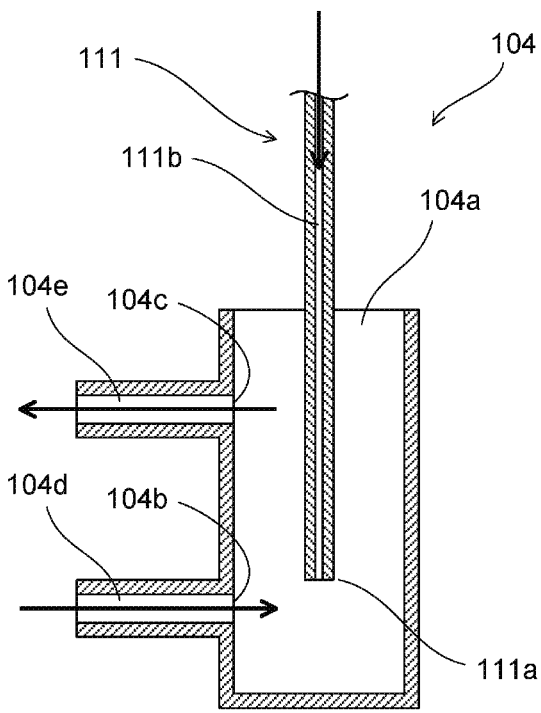
FIG. 9A
FIG. 9B
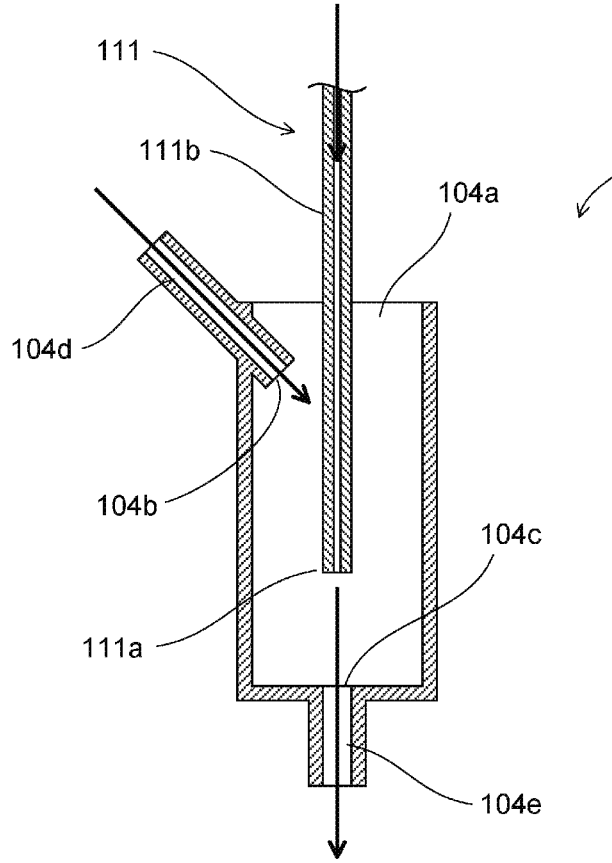
FIG. 9C

FIG. 12A    MEASUREMENT FOR BLOOD COAGULATION TEST
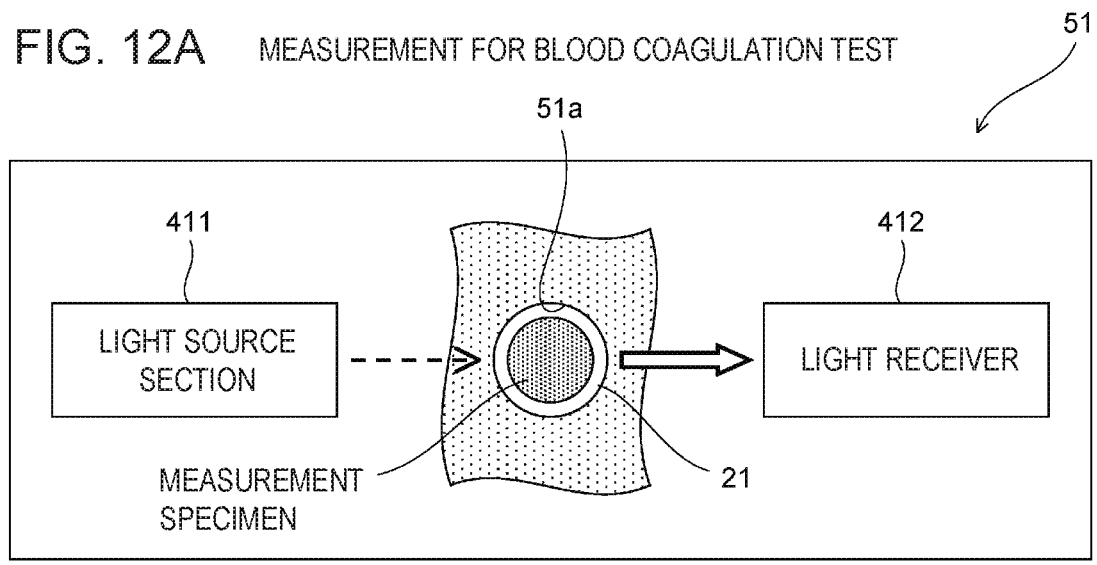
FIG. 12B    MEASUREMENT FOR IMMUNOLOGICAL TEST
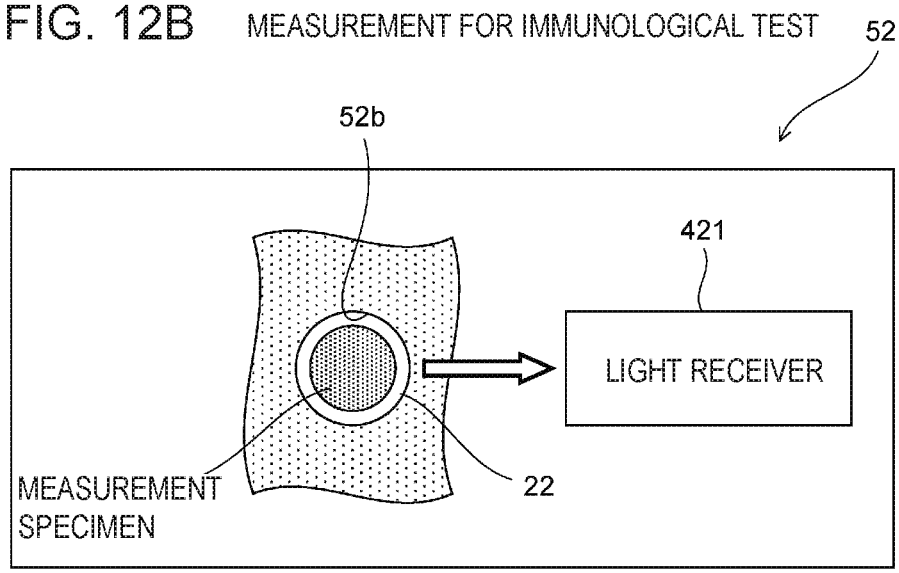

SAMPLE MEASUREMENT METHOD AND SAMPLE MEASUREMENT DEVICE

CROSS REFERENCE TO RELATED APPLICATIONS

This application claims priority based on 35 USC 119 from prior Japanese Patent Application No. 2017-253156 filed on Dec. 28, 2017, entitled "SAMPLE MEASUREMENT METHOD AND SAMPLE MEASUREMENT DEVICE", the entire contents of which are incorporated herein by reference.

BACKGROUND

The disclosure relates to a sample measurement method and a sample measurement device for measuring a sample.

There has been known a device that performs measurement for a blood coagulation test and measurement for an immunological test. For example, International Patent Application Publication No. WO 2013/187210 (Patent Literature 1) discloses an automatic analyzer including a blood coagulation time detector 501 that measures a coagulation time and an immune detector 502 that measures a heterogeneous immune item, as illustrated in FIG. 17. In this analyzer, a biological sample is dispensed into each of disposable reaction containers 505 from a sample disk 504 at a coagulation time sample dispensing position 503, and also reagents are dispensed into the disposable reaction containers 505 from reagent disks 506 and 507. Thereafter, a reaction container temperature adjusting block 508 adjusts the temperature of the disposable reaction container 505, and the blood coagulation time detector 501 measures the coagulation time. The disposable reaction containers 505 and the reaction container temperature adjusting block 508 are also used in the measurement of the heterogeneous immune item. In the measurement of the heterogeneous immune item, the measurement is performed by dispensing a reagent into the disposable reaction container 505 from a heterogeneous immune reagent disk 509.

However, in a device that performs measurement for a blood coagulation test as well as measurement for another test, no consideration has been made as to how to dispense a sample.

SUMMARY

A method according to one or more aspects may be a sample measurement method of performing first measurement for a blood coagulation test and second measurement for a test different from the blood coagulation test, including: dispensing a sample for use in the first measurement into a first container from a sample container; dispensing the sample for use in the second measurement into a second container different from the first container from the sample container from which the sample for use in the first measurement has been dispensed; performing the first measurement based on the sample dispensed into the first container; and performing the second measurement based on the sample dispensed into the second container.

A sample measurement device according to one or more aspects may include a first measurement section that performs first measurement for a blood coagulation test; a second measurement section that performs second measurement for a test different from the blood coagulation test; a dispensing mechanism unit that includes a nozzle capable of aspirating and discharging a sample and a drive section which lifts and lowers the nozzle, and that dispenses the sample from a sample container by using the nozzle; and a controller that performs control to cause the dispensing mechanism unit to lower the nozzle to aspirate a sample for use in the first measurement from the sample container by the lowered nozzle, lift the nozzle holding the aspirated sample, discharge the sample into a first container, and dispense the sample for use in the second measurement into a second container different from the first container from the sample container from which the sample for use in the first measurement has been aspirated.

A sample measurement device according to one or more aspects may include a first measurement section that performs first measurement for a blood coagulation test; a second measurement section that performs second measurement for a test different from the blood coagulation test; a dispensing mechanism unit that includes a nozzle capable of aspirating and discharging a sample and that dispenses the sample from a sample container by using the nozzle; and a controller that performs control to cause the dispensing mechanism unit to dispense the sample for use in the first measurement first from the sample container when there is a measurement order for the blood coagulation test.

BRIEF DESCRIPTION OF DRAWINGS

FIG. 1 is a flowchart illustrating a sample measurement method according to an embodiment;

FIG. 3 is a diagram illustrating a view of a configuration of a sample measurement device according to an embodiment;

FIG. 9A is a diagram schematically illustrating a cross-sectional view of a configuration of a cleaning tank according to a modified example, FIG. 9B is a diagram schematically illustrating a cross-sectional view of a configuration of a cleaning tank for cleaning a dispensing mechanism unit that aspirates a sample from a sample aspirating position on the right side according to an embodiment, and FIG. 9C is a diagram schematically illustrating a cross-sectional view of a configuration of a cleaning tank for cleaning a dispensing mechanism unit that aspirates a sample from a sample aspirating position on the right side according to a modified example;

FIG. 12A is a diagram schematically illustrating a view of a configuration of a first measurement section according to an embodiment, and FIG. 12B is a diagram schematically illustrating a view of a configuration of a second measurement section according to an embodiment;

DETAILED DESCRIPTION

Figure 2A:
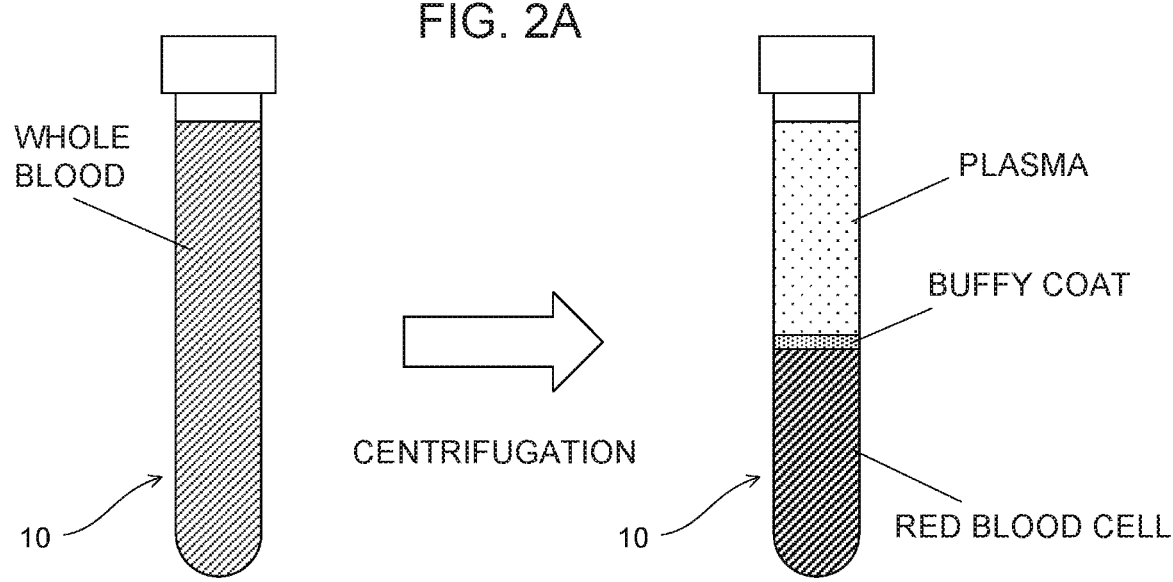
FIG. 2A is a diagram schematically illustrating a view of plasma separated in a sample container according to an embodiment.

A first aspect of the disclosure relates to a sample measurement method of performing first measurement for a blood coagulation test and second measurement for a test different from the blood coagulation test. The sample measurement method according to a first aspect includes: dispensing a sample for use in the first measurement into a first container (21) from a sample container (10) (S3, S16); dispensing the sample for use in the second measurement into a second container (21, 22) different from the first container (21) from the sample container (10) from which the sample for use in the first measurement has been dispensed (S6, S19); performing the first measurement based on the sample dispensed into the first container (21) (S4); and performing the second measurement based on the sample dispensed into the second container (21, 22) (S7).

A disease afflicting a subject may be analyzed in more detail based on a combination of the result of the first measurement for the blood coagulation test and the result of the second measurement for the test different from the blood coagulation test. For example, a disseminated intravascular coagulation syndrome (DIC) can be diagnosed based on a combination of a measurement result from a blood coagulation test and a measurement result from an immunological test. To be more specific, DIC diagnosis is performed based on a coagulation time acquired from the measurement result from the blood coagulation test, PIC and TAT acquired from the measurement result from the immunological test, and so on. Particularly when diagnosis is performed based on a combination of the result of the first measurement for the blood coagulation test and the result of the second measurement for the test different from the blood coagulation test as described above, both of the first measurement for the blood coagulation test and the second measurement for the test different from the blood coagulation test need to be performed properly.

Here, when whole blood is centrifuged, a layer of platelets and white blood cells, called a buffy coat, is formed between a plasma region and a red blood cell region in the sample container. The inventors have focused on the fact that mixing of the buffy coat into the sample affects the measurement for the blood coagulation test and may result in false positives in analysis based on the blood coagulation test-related measurement. As a result, the inventors have found out that, when aspiration of a sample for use in the measurement for the blood coagulation test is performed after aspiration of the sample for use in measurement for a test different from the blood coagulation test, the buffy coat is likely to be mixed into the sample for use in the blood coagulation test-related measurement.

In the sample measurement method according to a first aspect, the sample for use in the first measurement for the blood coagulation test is dispensed from the sample container before the sample for use in the second measurement for the test different from the blood coagulation test is dispensed from the sample container. Thus, the sample for use in the first measurement can be aspirated from the plasma region away from the buffy coat. As a result, the buffy coat can be inhibited from being mixed into the sample for use in the first measurement for the blood coagulation test. Therefore, the first measurement for the blood coagulation test can be properly performed. Since the sample measurement method according to a first aspect is capable of performing the first measurement for the blood coagulation test properly, more adequate diagnosis can be performed when the diagnosis is performed based on a combination of the result of the first measurement for the blood coagulation test and the result of the second measurement for the test different from the blood coagulation test.

In the sample measurement method according to a first aspect, the sample contained in the sample container (10) may include plasma separated from whole blood by centrifugation.

In the sample measurement method according to a first aspect, the whole blood contained in the sample container (10) is centrifuged (S1), and the plasma separated from the whole blood by centrifugation is dispensed as the sample into the first container (21) and the second container (21, 22) from the sample container (10) (S3, S6, S16, S19).

In the sample measurement method according to a first aspect, the sample container (10) contains plasma, a buffy coat, and red blood cells. When the whole blood is centrifuged, the respective components of the plasma, buffy coat, and red blood cells are stacked in this order from top to bottom in the sample container. When the plasma is aspirated in two steps from the sample container containing the three components as described above, the amount of the plasma is reduced by the first aspiration operation. As a result, there is a higher possibility of aspirating the buffy coat in the second aspiration operation. With the sample measurement method according to a first aspect, the sample for use in the first measurement is aspirated first, and thus the buffy coat is inhibited from being mixed into the sample for use in the first measurement. As a result, the first measurement for the blood coagulation test can be properly performed.

In the sample measurement method according to a first aspect, a nozzle (31) is inserted into a plasma region and aspirates the sample. This can ensure sample aspiration through the nozzle.

In the sample measurement method according to a first aspect, the nozzle (31) aspirates the sample with a tip (31*a*) of the nozzle (31) positioned above a central position of the plasma region. This can ensure sample aspiration through the nozzle and also suppress mixing of the buffy coat into the sample.

In the sample measurement method according to a first aspect, the nozzle (31) aspirates the sample with the nozzle (31) lowered by a predetermined amount from a liquid surface of the plasma region. This can ensure sample aspiration through the nozzle, and also allow the nozzle to be lowered to the extent that the tip of the nozzle does not reach the buffy coat. Thus, mixing of the buffy coat into the sample can be inhibited. Moreover, the sample is prevented from adhering to an outer peripheral surface of the nozzle. Thus, cleaning of the outer peripheral surface of the nozzle is facilitated. Furthermore, control of the nozzle can be simplified.

In this case, a drive section (37) that lifts and lowers the nozzle (31) is driven according to a lowering amount stored in a memory (61b, 62b) to lower the nozzle (31) by the predetermined amount from the liquid surface of the plasma region.

After a sensor (35) that senses that the tip (31a) of the nozzle (31) comes into contact with the liquid surface senses the liquid surface of the plasma region, the nozzle (31) is lowered by the predetermined amount from the liquid surface of the plasma region.

In the sample measurement method according to a first aspect, different nozzles (31, 431) are used to dispense the sample for use in the first measurement and to dispense the sample for use in the second measurement.

In the sample measurement method according to a first aspect, the same nozzle (31) is used to dispense the sample for use in the first measurement and to dispense the sample for use in the second measurement.

In the sample measurement method according to a first aspect, an inner peripheral surface and the outer peripheral surface of at least a part of the nozzle (31, 431), with which the sample has come into contact, are cleaned with a cleaning liquid. In this way, the nozzle for dispensing the sample is cleaned, and thus carry-over due to accidental mixing of another sample can be inhibited.

In the sample measurement method according to a first aspect, the sample container (10) is a blood collection tube.

In the sample measurement method according to a first aspect, the second measurement is measurement for an immunological test.

In the sample measurement method according to a first aspect, BF separation is performed to separate a liquid component from a test substance in the sample dispensed into the second container (21, 22). Since dispensing into the second container is performed after dispensing into the first container, the sample dispensed into the second container is more likely to be mixed with the buffy coat than the sample dispensed into the first container. In the sample measurement method according to a first aspect, the buffy coat mixed into the sample dispensed into the second container is removed by the BF separation. Thus, the second measurement for the immunological test can be properly performed.

In the sample measurement method according to a first aspect, the second measurement is measurement for a biochemical test.

A second aspect of the disclosure relates to a sample measurement device. The sample measurement device (100) according to a second aspect includes: a first measurement section (51) that performs first measurement for a blood coagulation test; a second measurement section (52) that performs second measurement for a test different from the blood coagulation test; a dispensing mechanism unit (30, 430) that includes a nozzle (31) capable of aspirating and discharging a sample and a drive section (37) which lifts and lowers the nozzle (31), and that dispenses the sample from a sample container (10) by using the nozzle (31); and a controller (61a, 62a) that performs control to cause the dispensing mechanism unit (30, 430) to lower the nozzle (31) to aspirate a sample for use in the first measurement from the sample container by the lowered nozzle (31), lift the nozzle (31) holding the aspirated sample, discharge the sample into a first container (21), and dispense the sample for use in the second measurement into a second container (21, 22) different from the first container (21) from the sample container (10) from which the sample for use in the first measurement has been aspirated.

The sample measurement device according to a second aspect achieves the same effects as those achieved in a first aspect.

The sample measurement device (100) according to a second aspect may further include a memory (61b, 62b) that stores a lowering amount of the nozzle (31), and the controller (61a, 62a) may be configured to drive the drive section (37) according to the lowering amount stored in the memory (61b, 62b) to lower the nozzle (31) by a predetermined amount from a liquid surface of the sample.

In this case, the drive section (37) is a stepping motor, and the memory (61b, 62b) stores the number of pulses corresponding to the lowering amount, and the controller (61a, 62a) may be configured to drive the drive section (37) according to the number of pulses stored in the memory (61b, 62b) to lower the nozzle (31) by the predetermined amount from the liquid surface of the sample.

The sample measurement device (100) according to a second aspect may further include a sensor (35) that senses that a tip (31a) of the nozzle (31) comes into contact with the liquid surface, and the controller (61a, 62a) may be configured to perform control to cause the dispensing mechanism unit (30, 430) to lower the nozzle (31) by the predetermined amount from the liquid surface of the sample after the sensor (35) senses that the tip (31a) of the nozzle (31) comes into contact with the liquid surface of the sample.

In the sample measurement device (100) according to a second aspect, the first measurement section (51) may include a light source section (411) that irradiates a measurement specimen with light and a light receiver (412) that receives light generated from the measurement specimen.

In the sample measurement device (100) according to a second aspect, the second measurement may be measurement for an immunological test.

In this case, the second measurement section (52) may include a light receiver (421) capable of photon counting. Thus, the second measurement section can perform highly sensitive and highly accurate measurement when performing measurement of chemiluminescence.

The second measurement section (52) may include a photomultiplier tube. Thus, the second measurement section can perform highly sensitive and highly accurate measurement when performing measurement of chemiluminescence.

In the sample measurement device (100) according to a second aspect, the second measurement may be measurement for a biochemical test.

In this case, the second measurement section (52) may include a light source section (411) that irradiates a measurement specimen with light and a light receiver (412) that receives light generated from the measurement specimen.

A third aspect of the disclosure relates to a sample measurement device. The sample measurement device (100) according to a third aspect includes: a first measurement section (51) that performs first measurement for a blood coagulation test; a second measurement section (52) that performs second measurement for a test different from the blood coagulation test; a dispensing mechanism unit (30, 430) that includes a nozzle (31) capable of aspirating and discharging a sample, and that dispenses the sample from a sample container (10) by using the nozzle (31); and a controller (61a, 62a) that performs control to cause the dispensing mechanism unit (30, 430) to dispense the sample for use in the first measurement first from the sample container (10) when there is a measurement order for the blood coagulation test.

In the sample measurement device according to a third aspect, the sample first dispensed from the sample container is used for the first measurement. The buffy coat is unlikely to be mixed into the sample dispensed first. Thus, the first measurement for the blood coagulation test can be properly performed.

In the sample measurement device (100) according to a third aspect , when a measurement order for the blood coagulation test and a measurement order for the test different from the blood coagulation test are set for a sample ID associated with the sample container (10), the controller (61a, 62a) may be configured to perform control to cause the dispensing mechanism unit (30, 430) to dispense the sample for use in the first measurement into a first container (21) from the sample container (10) and to dispense the sample for use in the second measurement into a second container (21, 22) different from the first container (21) from the sample container (10) from which the sample for use in the first measurement has been dispensed.

The sample measurement device (100) according to a third aspect may further include a transport unit (63) that transports a sample rack (101) carrying the sample container (10), thereby transporting the sample container (10) to an aspirating position (103a) for the dispensing mechanism unit (30, 430).

The disclosure may enable measurement for a blood coagulation test to be properly performed when performing the measurement for the blood coagulation test and measurement for a test different from the blood coagulation test.

Embodiments are explained with referring to drawings. In the respective drawings referenced herein, the same constituents are designated by the same reference numerals and duplicate explanation concerning the same constituents may be omitted. All of the drawings are provided to illustrate the respective examples only. No dimensional proportions in the drawings shall impose a restriction on the embodiments. For this reason, specific dimensions and the like should be interpreted with the following descriptions taken into consideration. In addition, the drawings include parts whose dimensional relationship and ratios are different from one drawing to another.

As illustrated in FIG. 1, a sample measurement method according to an embodiment is a sample measurement method including first measurement for a blood coagulation test and second measurement for a test different from the blood coagulation test. The sample measurement method according to an embodiment includes processing steps of Steps S1 to S7. For example, Step S1 is automatically performed with a centrifugal separator, while Steps S2 to S7 are automatically performed with a sample measurement device to be described later. Note that Steps S1 to S7 may be manually performed by an operator, respectively.

Figure 2B:
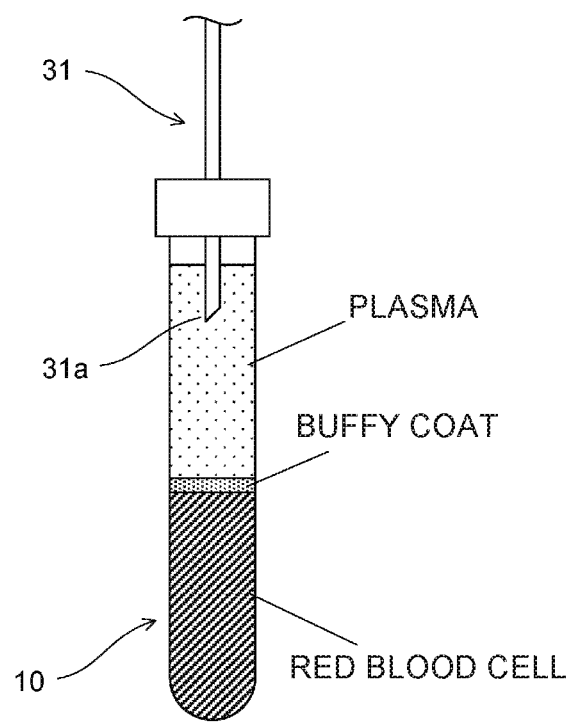
FIGS. 2B and 2C are diagrams illustrating views of aspiration of a sample from a sample container according to an embodiment.
Figure 2C:
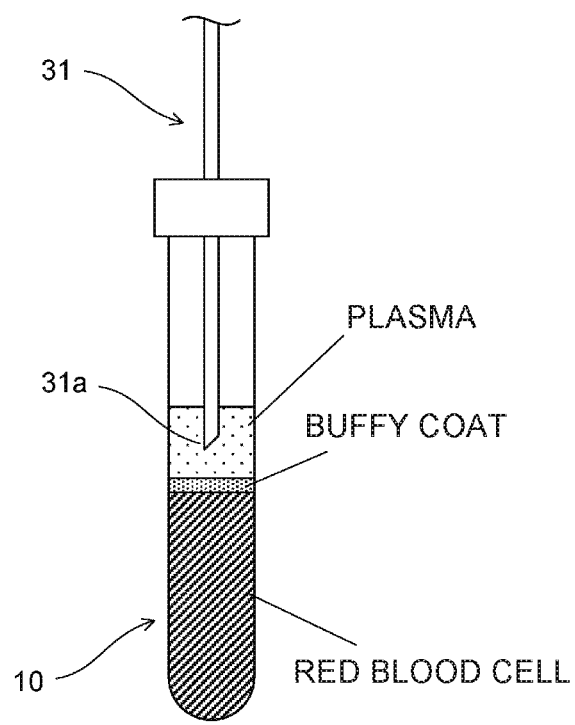

Prior to description of the respective steps illustrated in FIG. 1, description is given of a sample in a sample container 10 and aspiration of the sample from the sample container 10 with reference to FIGS. 2A to 2C.

As illustrated in the left part of FIG. 2A, the sample container 10 contains whole blood when blood is collected from a subject. Then, by performing centrifugation processing on the sample container 10 containing the whole blood, a plasma region and a red blood cell region, which are separated from the whole blood, are formed in the upper part and lower part of the sample container 10, respectively, as illustrated in the right part of FIG. 2A. The sample container 10 after the centrifugation as illustrated in the right part of FIG. 2A is fed to the sample measurement device. The sample in an embodiment is plasma separated inside the sample container 10.

Here, the inventors of the disclosure have focused on the fact that, following the centrifugation of the whole blood, a layer of platelets and white blood cells, called a buffy coat, is formed between the plasma region and the red blood cell region in the sample container 10. The right part of FIG. 2A schematically illustrates a state where respective components of the plasma, buffy coat, and red blood cells are stacked in this order from top to bottom in the sample container 10. The inventors have found out that, when aspiration of a sample (hereinafter referred to as the "first sample") for use in first measurement for a blood coagulation test is performed after aspiration of a sample (hereinafter referred to as the "second sample") for use in second measurement for a test different from the blood coagulation test, the buffy coat is likely to be mixed into the first sample. Then, the inventors have found out, as a problem, that mixing of the buffy coat into the first sample affects the first measurement for the blood coagulation test and may result in false positives in analysis based on the first measurement.

As illustrated in FIG. 2B, in the sample container 10 when fed to the sample measurement device, the liquid level of the plasma as the sample is well away from the buffy coat. In this case, the sample can be aspirated even when a tip 31a of a nozzle 31 for aspirating the sample is located at a position well away from the buffy coat. Therefore, the buffy coat components can be prevented from being mixed into the sample aspirated by the nozzle 31 when the sample is first aspirated from the sample container 10.

On the other hand, as illustrated in FIG. 2C, the liquid level of the plasma as the sample approaches the buffy coat after aspiration from the sample container 10 is performed once. In this case, aspiration of the sample needs to be performed by locating the tip 31a of the nozzle 31 at a position close to the buffy coat. Therefore, the buffy coat components are likely to be mixed into the sample aspirated by the nozzle 31 in the second time round of sample aspiration from the sample container 10.

As described above, the aspiration is performed at a position distant from the buffy coat in the first aspiration operation, and the aspiration is performed at a position close to the buffy coat in the second aspiration operation. For this reason, the buffy coat components are likely to be mixed into the aspirated sample in the second aspiration operation. Therefore, the buffy coat components are likely to be contained in the first sample when the aspiration for the first measurement is performed later. After exhaustive consideration made so as to properly perform the first measurement for the blood coagulation test, the inventors have decided to perform the aspiration for the first measurement first as illustrated in FIG. 2B. The procedure to do so is described below with reference to FIG. 1.

Referring back to FIG. 1, in Step S1, the sample container 10 containing the whole blood is subjected to centrifugation processing. Thus, the whole blood is centrifuged to separate the plasma as illustrated in the right part of FIG. 2A.

Then, it is determined in Step S2 whether or not a blood coagulation test-related measurement order is set for a target sample. More specifically, it is determined in Step S2 whether to perform the first measurement on the target sample. When the blood coagulation test-related measurement order is set for the target sample, that is, when the measurement order for the first measurement is set for the target sample, the first sample for use in the first measurement is dispensed into a first container from the sample container 10 in Step S3. Then, in Step S4, the first measurement is performed based on the first sample dispensed into the first container. On the other hand, when the measurement order for the first measurement is not set for the target sample, the processing in Steps S3 and S4 is skipped.

Thereafter, it is determined in Step S5 whether or not a measurement order for a test different from the blood coagulation test is set for the target sample. More specifically, it is determined in Step S5 whether to perform the second measurement on the target sample. When the measurement order for the test different from the blood coagulation test is set for the target sample, that is, when the measurement order for the second measurement is set for the target sample, the second sample for use in the second measurement is dispensed from the sample container 10 into a second container different from the first container in Step S6. Then, in Step S7, the second measurement is performed based on the second sample dispensed into the second container. On the other hand, when the measurement order for the second measurement is not set for the target sample, the processing in Steps S6 and S7 is skipped.

Note that the first and second containers may be the same kind of containers or may be different kinds of containers. The first measurement in Step S4 may be performed after the dispensing into the first container, while the second measurement in Step S7 may be performed after the dispensing into the second container. Therefore, the execution order of the first measurement and the second measurement is not limited to the order illustrated in FIG. 1.

When the plasma is aspirated in two steps from the sample container 10 containing three components including the plasma, buffy coat, and red blood cells as described above, the amount of the plasma is reduced by the first aspiration operation. As a result, there is a higher possibility of aspirating the buffy coat in the second aspiration operation. However, according to an embodiment, dispensing of the first sample for the first measurement is performed before dispensing of the second sample for the second measurement. More specifically, when the measurement order of the first measurement and the measurement order of the second measurement are both set for the target sample, the second sample for use in the second measurement is aspirated from the sample container 10 from which the first sample has been aspirated. Accordingly, the first sample can be aspirated from the plasma region away from the buffy coat. Thus, the buffy coat can be suppressed from being mixed into the first sample. As a result, the first measurement for the blood coagulation test can be properly performed.

Moreover, a disease afflicting the subject may be analyzed in more detail based on a combination of the result of the first measurement and the result of the second measurement. For example, a disseminated intravascular coagulation syndrome (DIC) can be diagnosed based on a combination of a measurement result from a blood coagulation test and a measurement result from an immunological test. To be more specific, DIC diagnosis is performed based on a coagulation time acquired from the measurement result from the blood coagulation test, PIC and TAT acquired from the measurement result from the immunological test, and the like. When the sample is dispensed and measured as illustrated in FIG. 1, the first measurement for the blood coagulation test can be properly performed. Thus, more adequate diagnosis can be performed based on a combination of the result of the first measurement and the result of the second measurement.

<Configuration of Sample Measurement Device>

A configuration of a sample measurement device 100 is described below.

As illustrated in FIG. 3, the sample measurement device 100 includes a first measurement unit 61, a second measurement unit 62, a transport unit 63, and an analysis unit 64. The first measurement unit 61 is communicably connected to the transport unit 63 and the analysis unit 64. The second measurement unit 62 is communicably connected to the analysis unit 64. In FIG. 3, X, Y, and Z axes are orthogonal to each other. An X-axis forward direction corresponds to a leftward direction, a Y-axis forward direction corresponds to a rearward direction, and a Z-axis forward direction corresponds to a vertically downward direction. Note that, in the other drawings, the X, Y, and Z axes are set in the same manner as FIG. 3.

The sample measurement device 100 analyzes a sample contained in a sample container 10 closed with a plug body 11. The sample container 10 houses the sample therein and has its top sealed with the plug body 11. The plug body 11 is made of elastic synthetic resin, for example.

The first measurement unit 61 includes a dispensing mechanism unit 30, a first measurement section 51, and a controller 61a. The dispensing mechanism unit 30 includes a nozzle 31 and an arm 32. The nozzle 31 is configured to be capable of penetrating through the plug body 11 and aspirating and discharging the sample. The nozzle 31 is an aspiration tube. The nozzle 31 is provided at an end of the arm 32, and the arm 32 is configured to be turnable. The dispensing mechanism unit 30 dispenses the sample into a reaction container 21 from the sample container 10 using the nozzle 31. The first measurement section 51 performs first measurement for a blood coagulation test. The controller 61a controls all the parts of the first measurement unit 61. The controller 61a also controls all the parts of the first measurement unit 61 such that they perform the processing illustrated in FIG. 1. The controller 61a includes a CPU and a microcomputer, for example.

The second measurement unit 62 includes a second measurement section 52 and a controller 62a. The second measurement section 52 performs second measurement for an immunological test. The immunological test-related measurement is measurement for a test different from the blood coagulation test. The immunological test-related measurement includes measurement of immunological analysis items, measurement by immunological reaction, and the like. The immunological test-related measurement is measurement using antigen-antibody reaction. The controller 62a controls all the parts of the second measurement unit 62. The controller 62a includes a CPU and a microcomputer, for example.

The transport unit 63 includes a mechanism to transport the sample container 10 to the first measurement unit 61. The analysis unit 64 includes a personal computer, for example. The analysis unit 64 includes a controller 64a. The controller 64a includes a CPU, for example.

When the sample container 10 is located at a predetermined position, the dispensing mechanism unit 30 turns the arm 32 to locate the nozzle 31 immediately above the sample container 10. Then, the dispensing mechanism unit 30 lowers the arm 32 to lower the nozzle 31. Thus, the tip of the nozzle 31 penetrates downward through the plug body 11. Thereafter, the dispensing mechanism unit 30 aspirates the sample in the sample container 10 through the tip of the nozzle 31. Once the sample is aspirated, the dispensing mechanism unit 30 lifts the arm 32 to lift the nozzle 31. Accordingly, the nozzle 31 is pulled out of the plug body 11. Subsequently, the dispensing mechanism unit 30 turns the arm 32 to locate the nozzle 31 immediately above the reaction container 21. The dispensing mechanism unit 30 lowers the arm 32 to insert the tip of the nozzle 31 into the reaction container 21. Then, the dispensing mechanism unit 30 discharges the sample aspirated from the sample container 10 into the reaction container 21.

When one sample is measured by both of the first and second measurement sections 51 and 52, the dispensing mechanism unit 30 dispenses the sample in the sample container 10 into two new reaction containers 21. To be more specific, the dispensing mechanism unit 30 aspirates the sample from the sample container 10 and repeats twice a dispensing operation of discharging the aspirated sample into the new reaction containers 21. The sample first dispensed into the reaction container 21 is the sample to be measured by the first measurement section 51, while the sample dispensed next into the reaction container 21 is the sample to be measured by the second measurement section 52. The reaction container 21 into which the sample is dispensed first is the first container, while the reaction container 21 into which the sample is dispensed next is the second container.

When one sample is measured only by the first measurement section 51, the dispensing mechanism unit 30 dispenses the sample in the sample container 10 into one new reaction container 21. When one sample is measured only by the second measurement section 52, the dispensing mechanism unit 30 dispenses the sample in the sample container 10 into one new reaction container 21.

The reaction container 21 is a container, so-called cuvette, having a top opening. The reaction container 21 is a disposable container for measurement by the first measurement section 51 in the first measurement unit 61.

The first measurement unit 61 transfers the reaction container 21 to the first measurement section 51, the reaction container 21 having the first sample dispensed thereinto for measurement by the first measurement section 51. In this event, the first measurement unit 61 prepares a measurement specimen by adding a predetermined reagent to the reaction container 21, and then transfers the reaction container 21 housing the measurement specimen to the first measurement section 51. The first measurement section 51 irradiates the measurement specimen in the reaction container 21 with light, and measures light transmitted through the measurement specimen or light scattered by the measurement specimen. The measurement principle for the first measurement section 51 is, for example, a coagulation method, a synthetic substrate method, immunonephelometry, an agglutination method, and the like. The controller 61a generates measurement data based on the light measured by the first measurement section 51.

The first measurement unit 61 transfers the reaction container 21 to the second measurement unit 62, the reaction container 21 having the second sample dispensed thereinto for measurement by the second measurement section 52. The second measurement unit 62 transfers the second sample in the reaction container 21, which is transferred from the first measurement unit 61, to a reaction container 22. The reaction container 22 is a container, so-called cuvette, having a top opening. The reaction container 22 is a disposable container for measurement by the second measurement section 52 in the second measurement unit 62. The second measurement unit 62 prepares a measurement specimen by adding a predetermined reagent to the reaction container 22 into which the second sample is dispensed, and then transfers the reaction container 22 housing the measurement specimen to the second measurement section 52. The second measurement section 52 measures light generated from the measurement specimen in the reaction container 22, that is, chemiluminescence based on a test substance contained in the second sample. The controller 62a generates measurement data based on the light measured by the second measurement section 52.

Here, the chemiluminescence is light emitted using energy generated by chemical reaction, for example, light emitted when molecules are excited by chemical reaction into an excited state and then return to the ground state. The chemiluminescence measured by the second measurement section 52 in an embodiment is light based on chemiluminescent enzyme immunoassay (CLEIA), which is light generated by reaction between an enzyme and a substrate. Note that the chemiluminescence measured by the second measurement section 52 may be, for example, light based on chemiluminescent immunoassay (CLIA), electrochemiluminescent immunoassay (ECLIA), fluorescent enzyme immunoassay (FEIA), luminescent oxygen channeling immunoassay (LOCI), bioluminescent enzyme immunoassay (BLEIA), or the like.

The controller 64a in the analysis unit 64 performs blood coagulation test-related analysis based on the measurement data generated by the first measurement unit 61. To be more specific, the controller 64a performs analysis for analysis items such as PT, APTT, Fbg, extrinsic coagulation factor, intrinsic coagulation factor, coagulation factor XIII, HpT, TTO, FDP, D-dimer, PIC, FM, ATIII, Plg, APL, PC, VWF:Ag, VWF:RCo, ADP, collagen, and epinephrine.

The controller 64a also performs immunological test-related analysis based on the measurement data generated by the second measurement unit 62. To be more specific, the controller 64a performs analysis for analysis items such as HBs antigen, HBs antibody, HBc antibody, HBe antigen, HBe antibody, HCV antibody, TP antibody, HTLV antibody, HIV antigen and antibody, TAT, PIC, TM, tPAI/c, TSH, FT3, and FT4.

Note that the second measurement unit 62 may perform measurement for a test different from the immunological test. For example, the second measurement unit 62 may perform biochemical test-related measurement. In this case, the controller 64a performs biochemical test-related analysis based on the measurement data generated by the second measurement unit 62. To be more specific, the controller 64a performs analysis for analysis items such as T-BIL, D-BIL, AST, ALT, ALP, LDH, γ-GTP, T-CHO, CRE, and CK. The second measurement unit 62 may also perform genetic test-related measurement.

Figure 4:
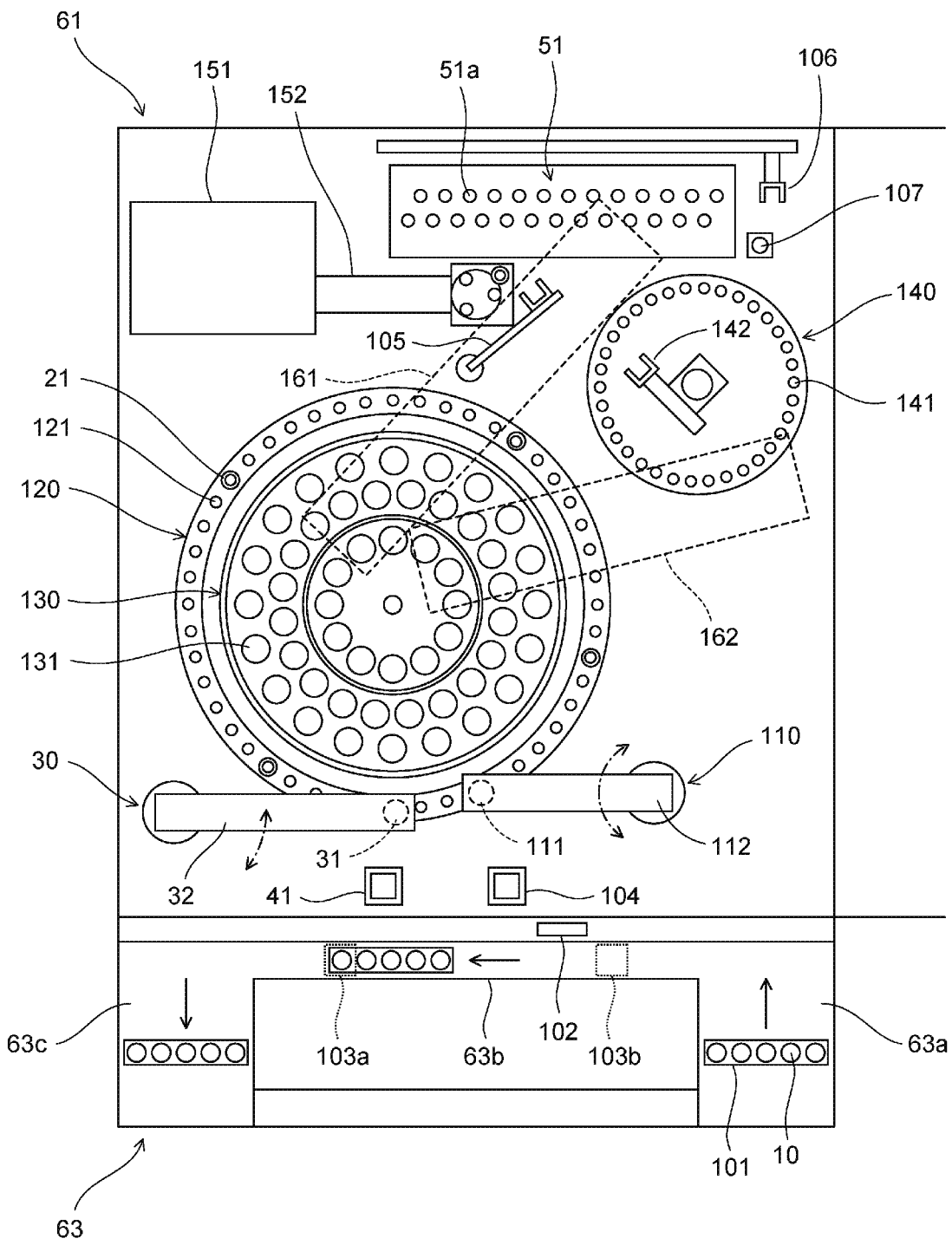
FIG. 4 is a diagram schematically illustrating a view of configurations of a first measurement unit and a transport unit according to an embodiment.

As illustrated in FIG. 4, the transport unit 63 includes a rack setting part 63a, a rack transporter 63b, and a rack collector 63c. The rack setting part 63a and the rack collector 63c are connected to the right end and left end of the rack transporter 63b, respectively. A bar code reader 102 is provided behind the rack transporter 63b. An operator installs a sample rack 101 having the sample containers 10 set therein in the rack setting part 63a.

Figure 5A:
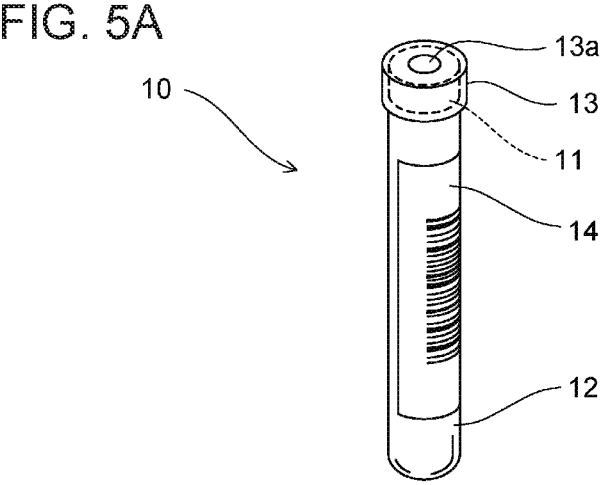
FIG. 5A is a diagram schematically illustrating a perspective view of a configuration of a sample container according to an embodiment.
Figure 5B:
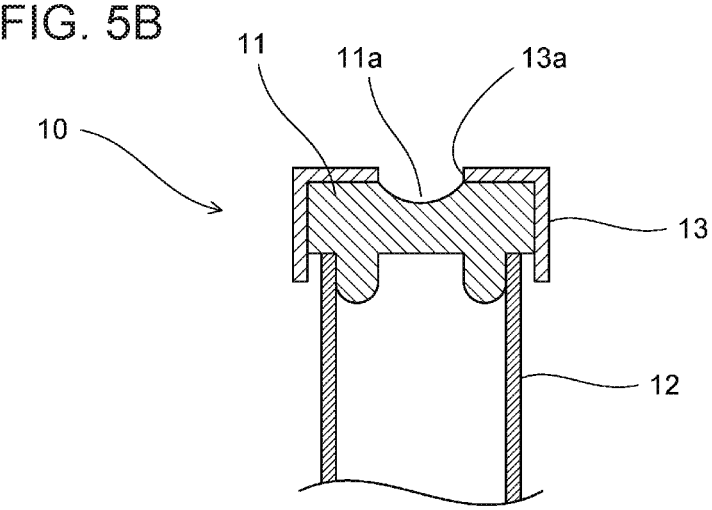
FIG. 5B is a diagram schematically illustrating a cross-sectional view of a configuration of a sample container according to an embodiment.

As illustrated in FIGS. 5A and 5B, the sample container 10 includes the plug body 11, a body part 12, a lid part 13, and a bar code label 14. The body part 12 is a blood collection tube made of translucent glass or synthetic resin, and houses a sample. The plug body 11 is made of elastic synthetic resin or the like as described above. The plug body 11 seals the opening in the upper end of the body part 12 housing the sample. The plug body 11 has a recess 11*a* formed in its upper surface. The lid part 13 is made of plastic and covers the plug body 11 from above, which is attached to the body part 12. A vertically penetrating hole 13*a* is formed in the center of the lid part 13. The bar code label 14 is attached to the side of the body part 12. A bar code indicating a sample ID is printed on the bar code label 14. The sample ID is information capable of individually identifying the sample.

Figure 5C:
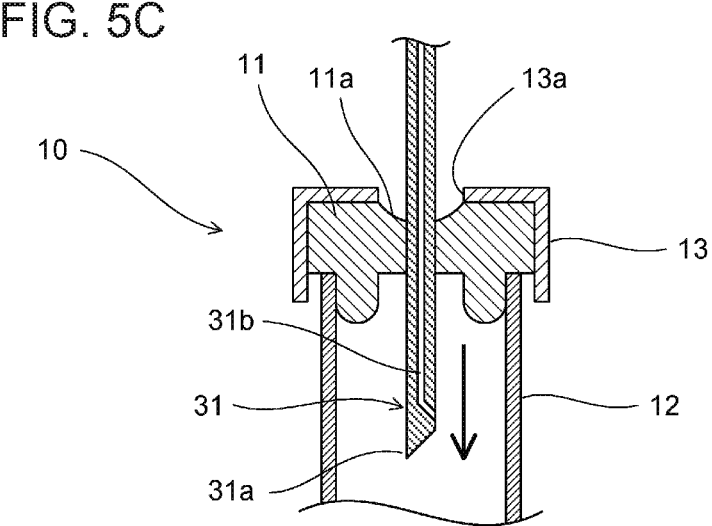
FIG. 5C is a diagram schematically illustrating a cross-sectional view of a state where a nozzle penetrates through a sample container according to an embodiment.

As illustrated in FIG. 5C, the nozzle 31 is a narrow rod-shaped member made of metal. The nozzle 31 has the sharp tip 31*a* that allows the nozzle 31 to easily penetrate through the plug body 11. A flow path 31*b* in the nozzle 31 extends vertically along with a direction in which the nozzle 31 extends, and is connected to the outside of the nozzle 31 from the side of the nozzle 31 near the tip 31*a*. When the nozzle 31 aspirates the sample in the sample container 10, the tip 31*a* of the nozzle 31 is located in the recess 11*a* of the plug body 11 through the hole 13*a* formed in the lid part 13. Then, as the nozzle 31 is moved downward, the tip 31*a* penetrates through the plug body 11, and the tip 31*a* of the nozzle 31 is located in the body part 12. Thus, the sample in the sample container 10 can be aspirated.

Referring back to FIG. 4, the transport unit 63 sends the sample rack 101 installed in the rack setting part 63*a* to the right end of the rack transporter 63*b* and further to in front of the bar code reader 102. The bar code reader 102 reads the bar code from the bar code label 14 on the sample container 10 to acquire the sample ID. The acquired sample ID is transmitted to the analysis unit 64 to acquire a measurement order for the sample.

Subsequently, the transport unit 63 transports the sample rack 101 carrying the sample containers 10 to sequentially locate the sample containers 10 at a sample aspirating position 103*a* or a sample aspirating position 103*b*. The sample aspirating position 103*a* is a position for the dispensing mechanism unit 30 to aspirate the sample, while the sample aspirating position 103*b* is a position for a dispensing mechanism unit 110 to be described later to aspirate the sample. Upon completion of the sample aspiration for all the sample containers 10 carried by the sample rack 101, the transport unit 63 transports the sample rack 101 to the rack collector 63*c*.

The first measurement unit 61 includes the dispensing mechanism units 30 and 110, cleaning tanks 41 and 104, a reaction container table 120, a reagent table 130, a heating table 140, a reaction container housing section 151, a reaction container feeder 152, transfer sections 105 and 106, reagent dispensers 161 and 162, the first measurement section 51, and a disposal port 107.

Figure 6:
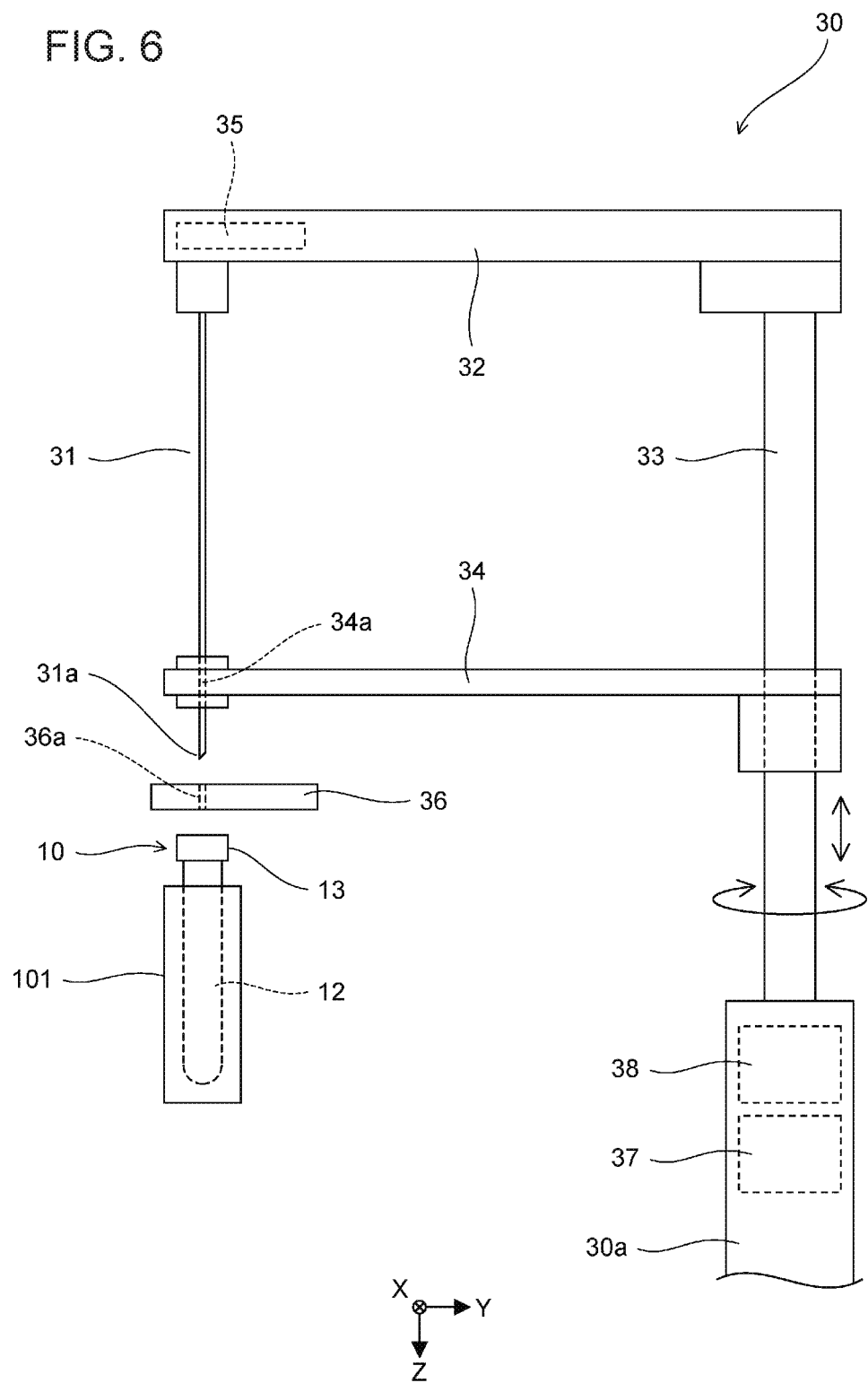
FIG. 6 is a diagram schematically illustrating a side view of a configuration of a dispensing mechanism unit according to an embodiment.

As illustrated in FIG. 6, the dispensing mechanism unit 30 includes a main body part 30*a*, the nozzle 31, the arm 32, a shaft part 33, a guide member 34, and a sensor 35. FIG. 6 illustrates, besides the dispensing mechanism unit 30, the sample container 10 located at the sample aspirating position 103*a* and a cleaner 36 provided immediately above the sample aspirating position 103*a*.

The main body part 30*a* includes a drive section 37 to move the shaft part 33 in the Z-axis direction and a drive section 38 to rotate the shaft part 33 about the Z-axis direction. The drive sections 37 and 38 each include a stepping motor. The shaft part 33 supports the arm 32. The nozzle 31 is installed facing downward at the end of the arm 32. The guide member 34 can be rotated along with the rotation of the shaft part 33, and is installed onto the shaft part 33 so as not to change the position in the Z-axis direction. The guide member 34 has a vertically penetrating hole 34*a* formed at its tip, and the nozzle 31 is inserted into this hole 34*a*. The hole 34*a* limits the movement direction of the nozzle 31 to the Z-axis direction. The sensor 35 is a sensor that senses the tip 31*a* of the nozzle 31 coming into contact with the liquid surface. The sensor 35 includes a capacitance sensor, for example.

The cleaner 36 has a vertically penetrating passage 36*a*. The cleaner 36 is arranged such that the nozzle 31 passes through the passage 36*a* when the nozzle 31 aspirates the sample from the sample container 10. The cleaner 36 performs basic cleaning of the nozzle 31 by discharging and aspirating a cleaning liquid inside when the nozzle 31 passes through the passage 36*a*.

Figure 7A:
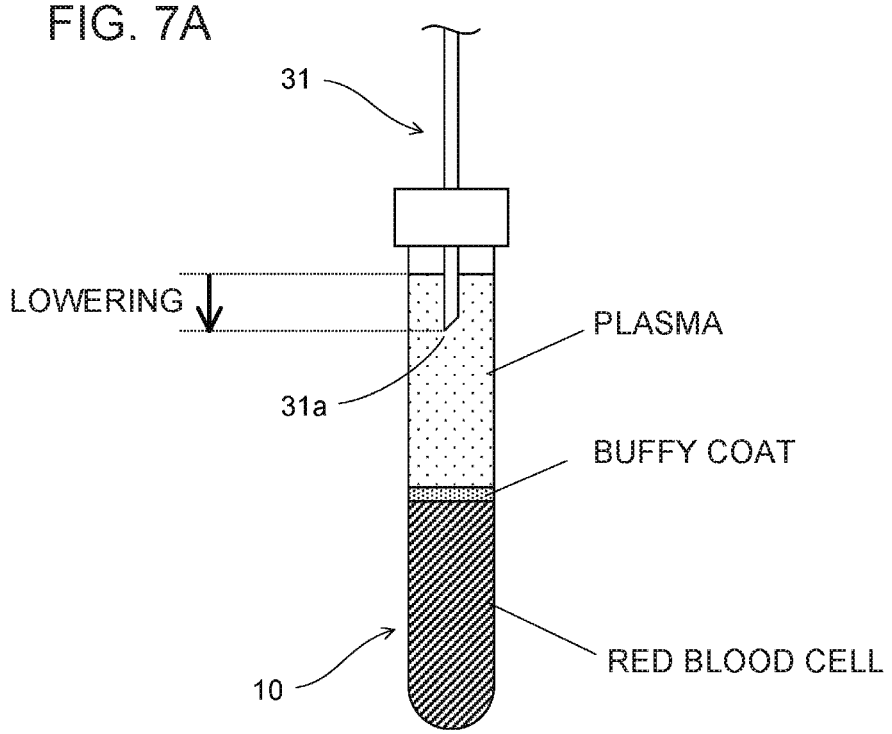
FIG. 7A is a diagram illustrating a schematic view of a lowering amount of a tip of a nozzle according to an embodiment.

During aspiration of the first sample, as illustrated in FIG. 7A, the controller 61*a* performs control to cause the dispensing mechanism unit 30 to lower the nozzle 31 to penetrate through the plug body 11 and then further keep lowering the nozzle 31. Then, the controller 61*a* detects, through the sensor 35, that the tip 31*a* of the nozzle 31 comes into the liquid surface of the plasma region. The controller 61*a* performs control to cause the dispensing mechanism unit 30 to aspirate the first sample by lowering the nozzle 31 by a predetermined amount after the tip 31*a* comes into contact with the liquid surface. The lowering amount of the nozzle 31 from the liquid surface in this case is determined based on a proportion of plasma contained in typical whole blood and the amount of the whole blood housed in the sample container 10, and is stored in a memory 61*b* to be described later. To be more specific, the lowering amount of the nozzle 31 from the liquid surface in this case is determined so as to locate the tip 31*a* above in the plasma region and also to prevent the nozzle 31 from performing idle aspiration. The memory 61*b* stores the number of pulses corresponding to the lowering amount, that is, the number of pulses required to lower the nozzle 31 by driving the drive section 37.

In this way, for aspiration of the first sample, the nozzle 31 is inserted up to the plasma region as illustrated in FIG. 7A to aspirate the first sample. This can ensure the aspiration of the first sample through the nozzle 31. Moreover, the first sample is aspirated in a state where the nozzle 31 is lowered by a predetermined amount from the liquid surface. This can ensure the aspiration of the first sample through the nozzle 31, and also allow the nozzle 31 to be lowered to the extent that the tip 31*a* of the nozzle 31 does not reach the buffy coat. Thus, mixing of the buffy coat into the first sample can be suppressed. Moreover, the sample is prevented from adhering to the outer peripheral surface of the nozzle 31. Thus, cleaning of the outer peripheral surface of the nozzle 31 is facilitated. Furthermore, control of the nozzle 31 by the controller 61*a* can be simplified.

Figure 7B:
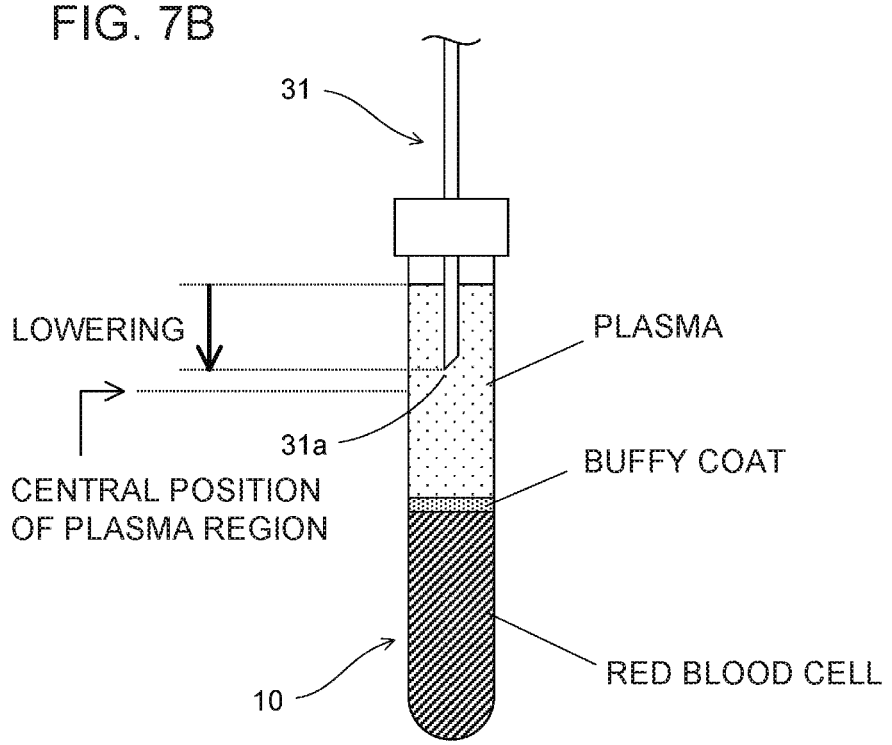
FIG. 7B is a schematic view illustrating a lowering amount of a tip of a nozzle according to a modified example.

Note that the lowering amount of the nozzle 31 from the liquid surface is not limited to the predetermined amount in FIG. 7A. For example, as illustrated in FIG. 7B, the controller 61*a* may perform control to cause the dispensing mechanism unit 30 to aspirate the first sample by locating the tip 31*a* above the central position of the plasma region after the tip 31*a* comes into contact with the liquid surface. In this case, the controller 61*a* acquires the central position of the plasma region, for example, by capturing an image of the sample container 10 with a camera installed on the side of the sample container 10 and analyzing the captured image. When the tip 31a is located above the central position of the plasma region to aspirate the first sample as described above, the aspiration of the first sample through the nozzle 31 can be ensured and mixing of the buffy coat into the first sample can be suppressed.

Referring back to FIG. 4, the dispensing mechanism unit 110 includes a nozzle 111 and an arm 112, as in the case of the dispensing mechanism unit 30, and has the same configuration as that illustrated in FIG. 6. Control of lowering the nozzle 111 is also performed in the same manner as the nozzle 31 in the dispensing mechanism unit 30.

The dispensing mechanism unit 30 aspirates the sample from the sample container 10 located at the sample aspirating position 103a. In this event, as described with reference to FIG. 5C, the nozzle 31 is driven downward so as to penetrate through the plug body 11, and a negative pressure is applied to the flow path 31b of the nozzle 31 to aspirate the sample into the flow path 31b. Thereafter, the nozzle 31 is driven upward and the tip 31a of the nozzle 31 is pulled out of the plug body 11. The dispensing mechanism unit 30 discharges the aspirated sample into a new reaction container 21 held on the reaction container table 120.

When the sample is dispensed directly from the sample container 10 through the nozzle 31, the operator can save the trouble of removing the plug body 11 of the sample container 10. Thus, the first measurement and the second measurement can be smoothly performed.

Here, as for the sample located at the sample aspirating position 103a, a measurement order to perform blood coagulation test-related measurement by the first measurement unit 61, a measurement order to perform immunological test-related measurement by the second measurement unit 62, or a measurement order to perform measurement by both of the measurement units is set.

When only the measurement order for the blood coagulation test is set, the dispensing mechanism unit 30 aspirates the sample once from the sample container 10 and discharges the aspirated sample into the reaction container 21 on the reaction container table 120 as a first sample for the blood coagulation test-related measurement. When only the measurement order for the immunological test is set, the dispensing mechanism unit 30 aspirates the sample once from the sample container 10 and discharges the aspirated sample into the reaction container 21 on the reaction container table 120 as a second sample for the immunological test-related measurement.

When the measurement order is set for both of the immunological test and the blood coagulation test, the dispensing mechanism unit 30 aspirates the sample in two steps from the sample container 10 and discharges the aspirated sample into different reaction containers 21 on the reaction container table 120. In this event, the dispensing mechanism unit 30 discharges the sample aspirated first into the reaction container 21 as the first sample for use in the blood coagulation test-related measurement, and discharges the sample aspirated later into the reaction container 21 as the second sample for use in the immunological test-related measurement.

Note that the dispensing mechanism unit 110 aspirates the sample, for which only the measurement order for the blood coagulation test is set, from the sample container 10 having its top not sealed with the plug body 11. The dispensing mechanism unit 110 discharges the aspirated sample into the reaction container 21 as the first sample for use in the blood coagulation test-related measurement.

The reaction container table 120 has a ring shape in a plan view and is located outside the reagent table 130. The reaction container table 120 is configured to be rotatable in the circumferential direction. The reaction container table 120 has holding holes 121 for holding the reaction containers 21.

The reaction container housing section 151 houses new reaction containers 21. The reaction container feeder 152 takes the reaction containers 21 one by one from the reaction container housing section 151 and feeds the reaction container 21 taken out to a grabbing position by the transfer section 105. The transfer section 105 grabs the reaction container 21 fed to the grabbing position by the reaction container feeder 152 and sets the reaction container 21 in the holding hole 121 in the reaction container table 120.

The cleaning tanks 41 and 104 are containers for cleaning the nozzles 31 and 111, respectively. The cleaning tank 41 makes up a part of a cleaning mechanism unit 40 to be described later. Upon completion of dispensing into one sample container 10 located at the sample aspirating position 103a, the dispensing mechanism unit 30 positions the nozzle 31 in the cleaning tank 41. The nozzle 31 positioned in the cleaning tank 41 is cleaned inside the cleaning tank 41. In this way, the nozzle 31 is cleaned inside the cleaning tank 41 for each sample. Likewise, the cleaning tank 104 also makes up a part of the same configuration as the cleaning mechanism unit 40. Upon completion of dispensing into one sample container 10 located at the sample aspirating position 103b, the dispensing mechanism unit 110 positions the nozzle 111 in the cleaning tank 104. The nozzle 111 positioned in the cleaning tank 104 is cleaned inside the cleaning tank 104. In this way, the nozzle 111 is cleaned inside the cleaning tank 104 for each sample.

Figure 8A:
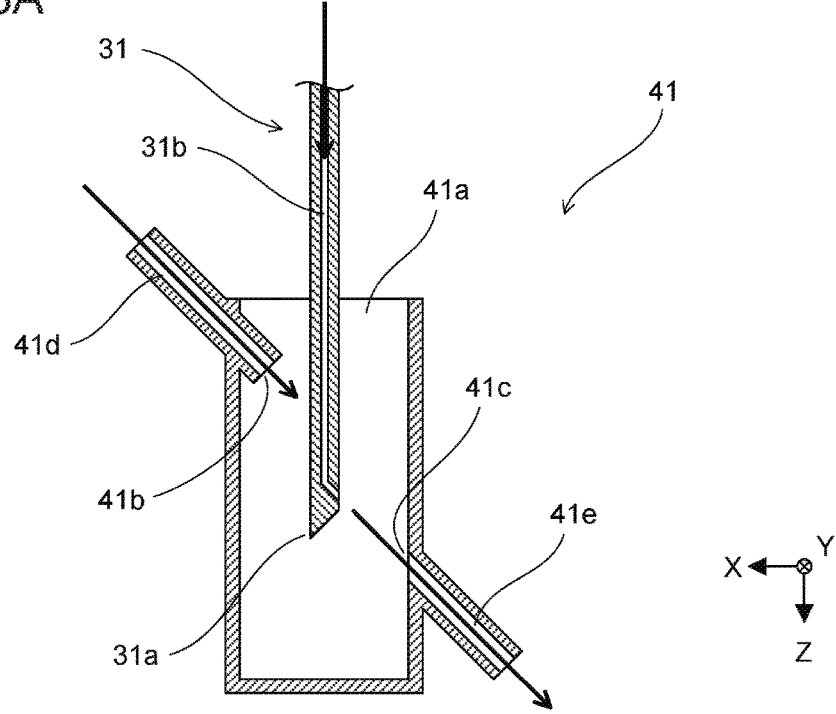
FIG. 8A is a diagram schematically illustrating a cross-sectional view of a configuration of a cleaning tank according to an embodiment.

As illustrated in FIG. 8A, the cleaning tank 41 is a container having the inside open through a top opening 41a. The cleaning tank 41 has an injection port 41b formed in its upper part and has a discharge port 41c formed in its lower part. The injection port 41b is connected to the outside of the cleaning tank 41 through an injection passage 41d. The discharge port 41c is connected to the outside of the cleaning tank 41 through a discharge passage 41e. The injection passage 41d is formed so as to face obliquely downward toward the injection port 41b, while the discharge passage 41e is formed so as to face obliquely upward toward the discharge port 41c.

In cleaning of the nozzle 31, the nozzle 31 is inserted into the cleaning tank 41 from above through the opening 41a. In this event, the nozzle 31 is inserted into the opening 41a in such a manner that the cleaning liquid injected from the injection port 41b spills out over the outer peripheral surface of at least a part of the nozzle 31 with which the sample has come into contact. Then, the cleaning liquid is injected into the cleaning tank 41 through the injection passage 41d and the injection port 41b, and is discharged through the discharge port 41c and the discharge passage 41e. Thus, the outer peripheral surface of the nozzle 31 is cleaned. The cleaning liquid also flows through the flow path 31b in the nozzle 31. The cleaning liquid in the flow path 31b is discharged from an outlet of the flow path 31b provided near the tip 31a. Accordingly, an inner peripheral surface of the nozzle 31, that is, the flow path 31b is cleaned. Thus, the inner and outer peripheral surfaces of at least a part of the nozzle 31, with which the sample has come into contact, are cleaned with the cleaning liquid.

Here, the flow path 31b of the nozzle 31 is cleaned at high pressure with the cleaning liquid. To be more specific, a flow rate of the cleaning liquid flowing through the flow path 31b is increased so as to generate a turbulent flow inside the flow path 31b. Generally, a turbulent flow is considered to be generated when the Reynolds number becomes greater than 4000. Assuming that fluid density is ρ, fluid flow rate is U, inside diameter of the flow path is d, and viscosity coefficient is μ, the Reynolds number Re is calculated according to the following equation.

$$Re = \rho U d / \mu$$

Figure 8B:
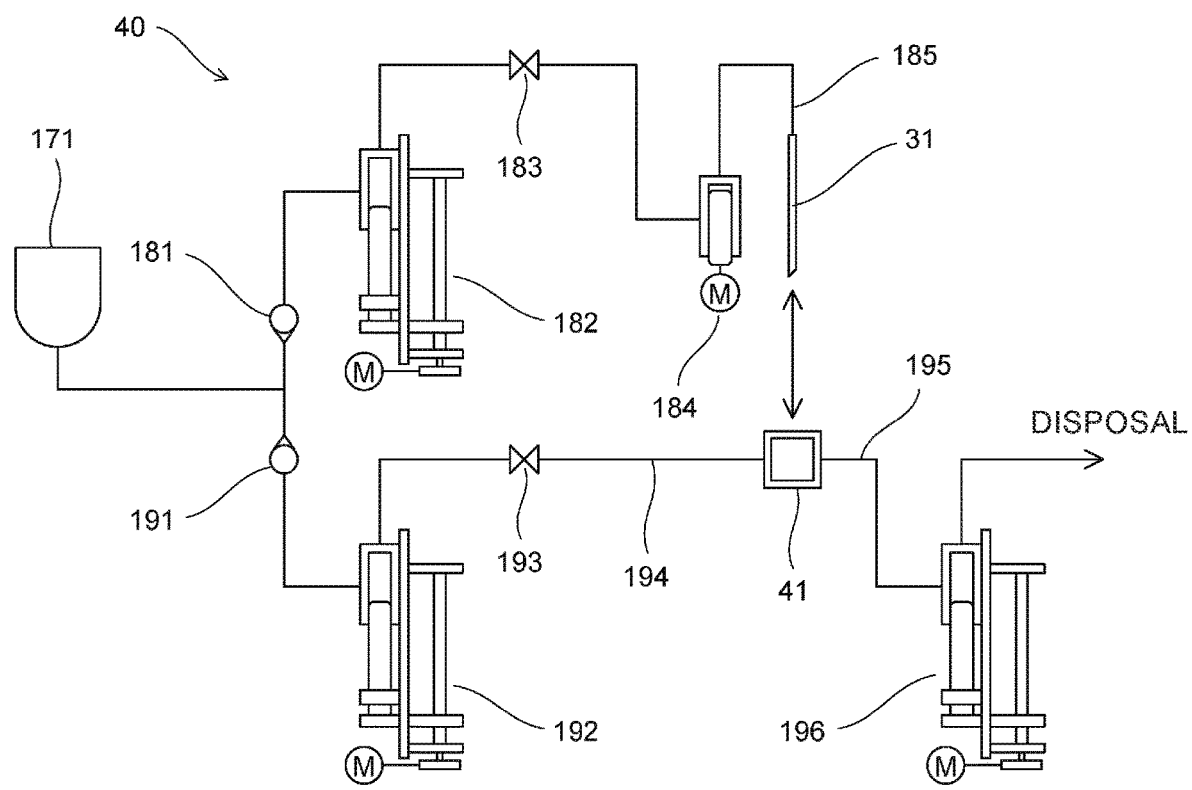
FIG. 8B is a diagram schematically illustrating a view of a configuration of a cleaning mechanism unit according to an embodiment.

With reference to FIG. 8B, a configuration of the cleaning mechanism unit 40 is described. As illustrated in FIG. 8B, the cleaning mechanism unit 40 includes a flow path and a mechanism to allow the cleaning liquid to flow through the flow path 31b of the nozzle 31, and a flow path and a mechanism to allow the cleaning liquid to flow into the cleaning tank 41.

The cleaning liquid is stored in a cleaning liquid chamber 171. The cleaning liquid chamber 171 is connected to a first pump 182 by a flow path through a check valve 181. The first pump 182 includes a syringe capable of sending the cleaning liquid at high pressure. The first pump 182 has its sending side connected to a metering syringe 184 by a flow path through a solenoid valve 183. The metering syringe 184 has its sending side connected to the flow path 31b of the nozzle 31 through a first flow path 185.

Meanwhile, the cleaning liquid chamber 171 is connected to a second pump 192 by a flow path through a check valve 191. The second pump 192 includes a syringe capable of sending the cleaning liquid. The second pump 192 has its sending side connected to the injection passage 41d and the injection port 41b of the cleaning tank 41 by a second flow path 194 through a solenoid valve 193. The discharge port 41c and the discharge passage 41e of the cleaning tank 41 are connected to a third pump 196 through a third flow path 195. The third pump 196 includes a syringe capable of applying a negative pressure to the third flow path 195. The third pump 196 has its sending side connected to a flow path for disposal of the cleaning liquid.

In dispensing the sample with the nozzle 31, the metering syringe 184 takes the sample into the flow path 31b by applying a negative pressure to the first flow path 185, and discharges the sample taken into the flow path 31b by applying a positive pressure to the first flow path 185.

In cleaning the flow path 31b of the nozzle 31, the first pump 182 takes in the cleaning liquid from the cleaning liquid chamber 171 in a state where the solenoid valve 183 is closed. Then, in a state where the solenoid valve 183 is opened, the first pump 182 allows the cleaning liquid taken in to flow into the flow path 31b of the nozzle 31 through the solenoid valve 183, the metering syringe 184, and the first flow path 185. In this event, the flow rate of the cleaning liquid flowing through the flow path 31b is set such that the Reynolds number Re expressed by the above equation becomes greater than 4000, and the first pump 182 is driven to realize this flow rate. Thus, a turbulent flow is generated in the flow path 31b to enhance the cleaning effect inside the flow path 31b. Moreover, cleaning inside the nozzle 31 can be ensured, and thus carry-over due to mixing of different samples through the nozzle 31 can be avoided.

Note that the lower end of the flow path 31b of the nozzle 31 is connected to the outer side surface of the nozzle 31 as illustrated in FIG. 8A, in order to prevent fragments of the plug body 11 from clogging the flow path 31b when the nozzle 31 penetrates through the plug body 11 of the sample container 10. Accordingly, the cleaning liquid flowing through the flow path 31b is discharged to the side of the nozzle 31. The discharge passage 41e for discharging the cleaning liquid extends obliquely downward. In this way, the direction of the cleaning liquid discharged from the flow path 31b coincides with the direction of the discharge passage 41e. Thus, the cleaning liquid discharged from the flow path 31b is smoothly collected to the discharge passage 41e through the discharge port 41c.

To clean the outer peripheral surface of the nozzle 31, the second pump 192 takes in the cleaning liquid from the cleaning liquid chamber 171 in a state where the solenoid valve 193 is closed. Then, in a state where the solenoid valve 193 is opened, the second pump 192 allows the cleaning liquid taken in to flow into the cleaning tank 41 from the injection port 41b of the cleaning tank 41 through the solenoid valve 193 and the second flow path 194. The flow rate of the cleaning liquid flowing through the second flow path 194 is set so as to be just adequate to enable cleaning of the outer peripheral surface of the nozzle 31. When the cleaning liquid flows into the cleaning tank 41, the third pump 196 is driven to draw the cleaning liquid into the third flow path 195 from the discharge port 41c and the discharge passage 41e. The third pump 196 allows the cleaning liquid drawn into the third flow path 195 to flow into a flow path for disposal.

As illustrated in FIG. 8B, the configuration of the cleaning mechanism unit 40 enables smooth cleaning of the inner and outer peripheral surfaces of the nozzle 31. The immunological test-related measurement is likely to have carry-over problem and has a high carry-over avoidance level. With the above configuration, the nozzle 31 that dispenses the sample is cleaned with the cleaning mechanism unit 40. Thus, the influence of carry-over can be suppressed in the immunological test-related measurement. Therefore, the immunological test-related measurement can be properly performed.

Note that the cleaning tank 41 illustrated in FIG. 8A may be configured as illustrated in FIG. 9A. More specifically, in a cleaning tank 41 illustrated in FIG. 9A, an injection port 41b is formed in the lower part of the cleaning tank 41, and an injection passage 41d is formed so as to face obliquely upward toward the injection port 41b. A discharge port 41c is formed in the upper part of the cleaning tank 41, and a discharge passage 41e is formed so as to face obliquely downward toward the discharge port 41c. In this case, the outer peripheral surface of the nozzle 31 is cleaned by discharging the cleaning liquid, which is injected from the injection port 41b, from the discharge port 41c.

As illustrated in FIG. 9B, a cleaning tank 104 is a container having its top open through an opening 104a. The cleaning tank 104 has an injection port 104b formed in its lower part and has a discharge port 104c formed in its upper part. The injection port 104b is connected to the outside of the cleaning tank 104 through an injection passage 104d. The discharge port 104c is connected to the outside of the cleaning tank 104 through a discharge passage 104e. The injection passage 104d and the discharge passage 104e are formed so as to extend in a horizontal direction. A tip 111a of the nozzle 111 is not sharp, and a flow path 111b inside the nozzle 111 extends in a vertical direction.

To clean the nozzle 111, the nozzle 111 is inserted into the cleaning tank 104 from above through the opening 104a. Then, the cleaning liquid is injected into the cleaning tank 104 through the injection passage 104d and the injection port 104b and discharged through the discharge port 104c and the discharge passage 104e. Thus, the outer peripheral surface of the nozzle 111 is cleaned. Moreover, the cleaning liquid flows through the flow path 111b inside the nozzle 111. Thus, the inner peripheral surface of the nozzle 111, that is, the flow path 111b is cleaned.

As for the cleaning tank 104 and the nozzle 111, the same flow paths and mechanism as those in the case of the cleaning tank 41 and the nozzle 31 illustrated in FIG. 8B are formed. Except, as described above, the nozzle 111 dispenses a sample for use in blood coagulation test-related measurement only. A carry-over level in the blood coagulation test-related measurement is lower than that in the immunological test-related measurement. Therefore, in the case of the cleaning tank 104 and the nozzle 111, the first pump may be omitted from the same flow paths and mechanism as those illustrated in FIG. 8B, and a metering syringe may be used to flow the cleaning liquid through the flow path 111b.

Alternatively, the cleaning tank 104 may be configured as illustrated in FIG. 9C. More specifically, in a cleaning tank 104 illustrated in FIG. 9C, an injection port 104b and an injection passage 104d are configured in the same manner as the injection port 41b and the injection passage 41d in FIG. 8A. Also, a discharge port 104c is formed in the bottom of the cleaning tank 104, and a discharge passage 104e extends downward. When a flow path 111b linearly extends downward in the same manner as the nozzle 111, the cleaning liquid flowing through the flow path 111b is discharged downward. Thus, the downward extending discharge passage 104e achieves smooth collection of the cleaning liquid.

Referring back to FIG. 4, the heating table 140 includes holding holes 141 for holding the reaction containers 21 and a transfer section 142 that transfers the reaction containers 21. The heating table 140 has a circular shape in a plan view and is configured to be rotatable in the circumferential direction. The heating table 140 heats the reaction container 21 set in the holding hole 141 to 37° C.

When a first sample is discharged into a new reaction container 21 held on the reaction container table 120, the reaction container table 120 is rotated and the reaction container 21 housing the first sample is transferred to near the heating table 140. Then, the transfer section 142 of the heating table 140 grabs the reaction container 21 and sets the reaction container 21 in the holding hole 141 in the heating table 140. On the other hand, when a second sample is discharged into a new reaction container 21 held on the reaction container table 120, the reaction container table 120 is rotated and the reaction container 21 housing the second sample is transferred to near the heating table 140. Then, the transfer section 142 of the heating table 140 grabs the reaction container 21 to transfer the reaction container 21 to a holding hole 201a to be described later with reference to FIG. 10.

The reagent table 130 is configured to be capable of installing reagent containers 131 each housing a corresponding one of an adjusting reagent and a trigger reagent for use in blood coagulation test-related measurement. The reagent table 130 is configured to be rotatable in the circumferential direction. The reagent dispensers 161 and 162 dispense the reagent into the reaction containers 21 heated by the heating table 140.

To dispense the adjusting reagent into the reaction container 21, the transfer section 142 of the heating table 140 takes the reaction container 21 out of the holding hole 141 in the heating table 140 and sets the reaction container 21 at a predetermined position. Then, the reagent dispenser 161 or 162 aspirates the adjusting reagent from the reagent container 131 and discharges the aspirated adjusting reagent into the reaction container 21. Accordingly, the adjusting reagent is mixed into the sample. Thereafter, the transfer section 142 sets the reaction container 21 again in the holding hole 141 in the heating table 140.

To dispense the trigger reagent into the reaction container 21, the transfer section 106 takes the reaction container 21 out of the holding hole 141 in the heating table 140 and sets the reaction container 21 at a predetermined position. Then, the reagent dispenser 161 or 162 aspirates the trigger reagent from the reagent container 131 and discharges the aspirated trigger reagent into the reaction container 21. Accordingly, the trigger reagent is mixed into the sample to prepare a measurement specimen. Thereafter, the transfer section 106 sets the reaction container 21 in a holding hole 51a in the first measurement section 51.

The first measurement section 51 includes the holding holes 51a. The first measurement section 51 irradiates the reaction container 21 set in the holding hole 51a with light, and measures light transmitted through the measurement specimen or light scattered by the measurement specimen. Upon completion of the measurement of the measurement specimen in the reaction container 21, the reaction container 21 is disposed of through the disposal port 107 by the transfer section 106.

Figure 10:
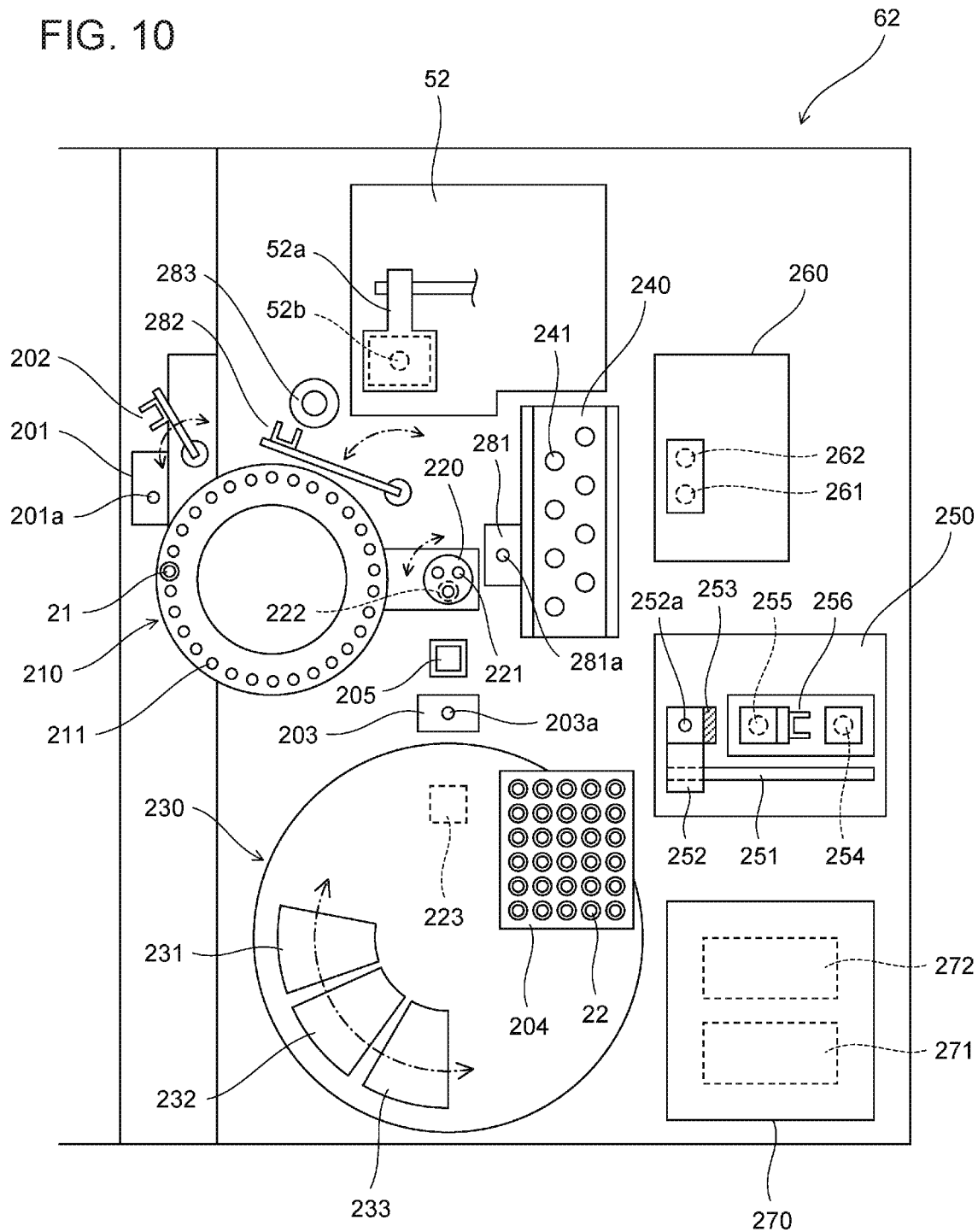
FIG. 10 is a diagram schematically illustrating a view of a configuration of a second measurement unit according to an embodiment.

As illustrated in FIG. 10, the second measurement unit 62 includes a member 201, a transfer section 202, handover tables 210 and 220, a member 203, a reaction container rack 204, a reagent table 230, a cleaning tank 205, a heater 240, a BF separator 250, a reagent dispenser 260, a reagent housing section 270, a member 281, a transfer section 282, a disposal port 283, and the second measurement section 52.

The member 201 includes a holding hole 201a for holding the reaction container 21. The transfer section 142 in the first measurement unit 61 takes the reaction container 21 housing a second sample out of the holding hole 121 in the reaction container table 120, and sets the reaction container 21 in the holding hole 201a in the member 201. The handover table 210 includes holding holes 211. The handover table 210 has a circular shape in a plan view and is configured to be rotatable in the circumferential direction. The transfer section 202 takes the reaction container 21 out of the holding hole 201a and sets the reaction container 21 in the holding hole 211 in the handover table 210.

Figure 11:
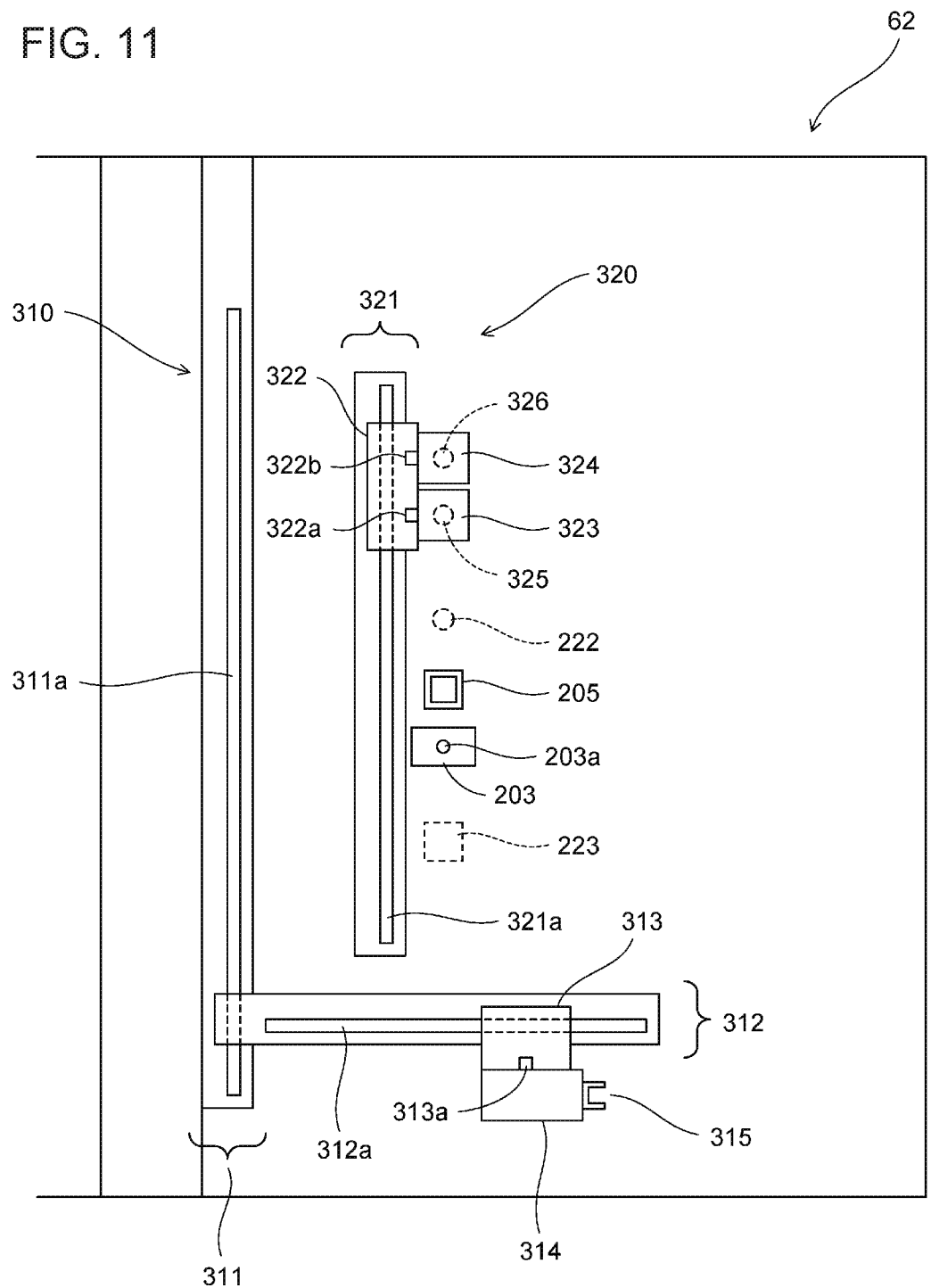
FIG. 11 is a diagram schematically illustrating a view of configurations of a transfer section and a dispensing section in a second measurement unit according to an embodiment.

Here, the second measurement unit 62 includes a transfer section 310 and a dispenser 320 illustrated in FIG. 11, in addition to the parts illustrated in FIG. 10. The transfer section 310 is installed on a wall surface in the first measurement unit 61, which is parallel to the Y-Z plane, while the dispenser 320 is installed on a ceiling surface of the second measurement unit 62.

As illustrated in FIG. 11, the transfer section 310 includes a forward-backward transfer section 311, a horizontal transfer section 312, a vertical transfer section 313, a support member 314, and a grabber 315. The forward-backward transfer section 311 drives a stepping motor to transfer the horizontal transfer section 312 in the Y-axis direction along a rail 311a extending in the Y-axis direction. The horizontal transfer section 312 drives a stepping motor to transfer the vertical transfer section 313 in the X-axis direction along a rail 312a extending in the X-axis direction. The vertical transfer section 313 drives a stepping motor to transfer the support member 314 in the Z-axis direction along a rail 313a extending in the Z-axis direction. The support member 314 is provided with the grabber 315. The grabber 315 is configured to be capable of grabbing the reaction containers 21 and 22.

The transfer section 310 drives the forward-backward transfer section 311, the horizontal transfer section 312, and the vertical transfer section 313 to transfer the grabber 315 in the X-axis, Y-axis, and Z-axis directions within the second measurement unit 62. Thus, the reaction containers 21 and 22 can be transferred within the second measurement unit 62.

The dispenser 320 includes a forward-backward transfer section 321, a vertical transfer section 322, support members 323 and 324, and nozzles 325 and 326. The forward-backward transfer section 321 drives a stepping motor to transfer the vertical transfer section 322 in the Y-axis direction along a rail 321a extending in the Y-axis direction. The vertical transfer section 322 drives a stepping motor to transfer the support member 323 in the Z-axis direction along a rail 322a extending in the Z-axis direction and to transfer the support member 324 in the Z-axis direction along a rail 322b extending in the Z-axis direction.

The nozzles 325 and 326 are installed in the support members 323 and 324, respectively, so as to line up in the Y-axis direction. The nozzles 325 and 326 extend in the Z-axis direction and have their tips pointed in the Z-axis forward direction. The nozzle 325 is used to dispense a sample, while the nozzle 326 is used to dispense a reagent.

As illustrated in FIG. 11, the nozzles 325 and 326, a sample aspirating position 222, the cleaning tank 205, a holding hole 203a, and a reagent aspirating position 223 are located in the same position in the X-axis direction. In other words, these members and positions are arranged in one straight line parallel to the Y-axis direction when seen in the Z-axis direction. Thus, the nozzles 325 and 326 can be located in the sample aspirating position 222, the cleaning tank 205, the holding hole 203a, and the reagent aspirating position 223 just by moving the nozzles 325 and 326 in the Y-axis direction without a mechanism to move the nozzles 325 and 326 in the X-axis direction. Thus, the configuration of the dispenser 320 can be simplified. Moreover, since the nozzles 325 and 326 can be cleaned with one cleaning tank 205, the cleaning tank 205 can be shared by the nozzles 325 and 326.

Note that flow paths inside the nozzles 325 and 326 extend in the vertical direction as in the case of the nozzle 111 in FIG. 9C. Therefore, the cleaning tank 205 also has the same shape as that of the cleaning tank 104 in FIG. 9C. In this case, the same mechanism and flow paths as those in FIG. 8B are configured to flow the cleaning liquid into the nozzles 325 and 326 and the cleaning tank 205. Moreover, the first pump is driven to flow the cleaning liquid into the nozzles 325 and 326 so that turbulent flows are generated inside the nozzles 325 and 326 during cleaning.

Referring back to FIG. 10, when a reaction container 21 is set in the holding hole 211 in the handover table 210, the transfer section 310 takes the reaction container 21 out of the holding hole 211 and sets the reaction container 21 in the holding hole 221 in the handover table 220. The handover table 220 includes three holding holes 221. The handover table 220 has a circular shape in a plan view and is configured to be rotatable in the circumferential direction. When the reaction container 21 is set in the holding hole 221 in the handover table 220, the handover table 220 is rotated in the circumferential direction to set the reaction container 21 in the sample aspirating position 222.

The reaction container rack 204 houses thirty new reaction containers 22. The member 203 includes a holding hole 203a for holding the reaction container 22.

The transfer section 310 takes the reaction container 22 out of the reaction container rack 204 and sets the reaction container 22 in the holding hole 203a. Then, the dispenser 320 uses the nozzle 325 to aspirate the second sample in the reaction container 21 set in the sample aspirating position 222 and discharge the aspirated second sample into the reaction container 22 set in the holding hole 203a. Thus, the second sample is transferred from the reaction container 21 to the reaction container 22. After the second sample is transferred, the nozzle 325 is cleaned in the cleaning tank 205. The reaction container 21 after completion of transferring of the second sample is disposed of through the disposal port 283 by the transfer section 282.

The reagent table 230 is configured to be capable of installing reagent containers 231 to 233 each housing a reagent for use in immunological test-related measurement. The reagent table 230 is configured to be rotatable in the circumferential direction. The reagent container 231 houses R1 reagent, the reagent container 232 houses R2 reagent, and the reagent container 233 houses R3 reagent.

The transfer section 310 takes the reaction container 22 housing the second sample out of the holding hole 203a and sets the reaction container 22 above the cleaning tank 205. In this state, the dispenser 320 uses the nozzle 326 to aspirate R1 reagent from the reagent container 231 set in the reagent aspirating position 223 and discharge the aspirated R1 reagent into the reaction container 22 set above the cleaning tank 205. After R1 reagent is dispensed, the nozzle 326 is cleaned in the cleaning tank 205.

The heater 240 includes holding holes 241 for heating the reaction container 22. The transfer section 310 sets the reaction container 22 having R1 reagent discharged thereinto in the holding hole 241 of the heater 240. After the reaction container 22 is heated for a predetermined time by the heater 240, the transfer section 310 takes the reaction container 22 out of the holding hole 241 and sets the reaction container 22 above the cleaning tank 205. In this state, the dispenser 320 uses the nozzle 326 to aspirate R2 reagent from the reagent container 232 set in the reagent aspirating position 223 and discharge the aspirated R2 reagent into the reaction container 22 set above the cleaning tank 205. After R2 reagent is dispensed, the nozzle 326 is cleaned in the cleaning tank 205.

The transfer section 310 sets the reaction container 22 having R2 reagent discharged thereinto in the holding hole 241 of the heater 240. After the reaction container 22 is heated for a predetermined time by the heater 240, the transfer section 310 takes the reaction container 22 out of the holding hole 241 and transfers the reaction container 22 to the BF separator 250.

Here, R1 reagent contains a capturing substance to be connected with the test substance. R2 reagent contains magnetic particles. When R1 reagent and R2 reagent are discharged into the reaction container 22 and the reaction container 22 is heated by the heater 240, the test substance contained in the second sample in the reaction container 22 is connected with the magnetic particles through the capturing substance by antigen-antibody reaction. As a result, a composite in which the test substance and the magnetic particles are connected with each other is generated.

The BF separator 250 includes a rail 251 extending in the X-axis direction, a support member 252 that moves along the rail 251, a magnet 253 installed on the support member 252, a nozzle 254 for aspirating a liquid component in the reaction container 22, a nozzle 255 for discharging the cleaning liquid, and a grabber 256 for grabbing the reaction container 22. The BF separator 250 also includes a mechanism to transfer the support member 252 in the X-axis direction along the rail 251 and a mechanism to transfer the nozzles 254 and 255 and the grabber 256 in the Z-axis direction.

The transfer section 310 sets the reaction container 22 heated after discharging of R2 reagent in a holding hole 252a provided in the support member 252. The magnet 253 is positioned near the X-axis negative side of the holding hole 252a. Thus, in the reaction container 22 set in the holding hole 252a, the composite is drawn to a wall surface of the reaction container 22 on the X-axis negative side.

Subsequently, the reaction container 22 set in the holding hole 252a is positioned immediately below the nozzle 254. The nozzle 254 removes the liquid component from the reaction container 22. Then, the reaction container 22 set in the holding hole 252a is positioned immediately below the nozzle 255. The nozzle 255 discharges a cleaning liquid into the reaction container 22. Thereafter, the grabber 256 takes the reaction container 22 out of the holding hole 252a and agitates the reaction container 22 taken out through vibration. Upon completion of the agitation, the grabber 256 returns the reaction container 22 to the holding hole 252a. Then, the nozzle 254 removes the liquid component from the reaction container 22. The BF separator 250 repeats such operations.

Note that the BF separator 250 includes an unillustrated cleaning tank for cleaning the nozzle 254. This cleaning tank is positioned immediately below the nozzle 254 and has the same configuration as that of the cleaning tank 41 in FIG. 9A. The same mechanism and flow paths as those in FIG. 8B are configured to flow the cleaning liquid into the nozzle 254 and the cleaning tank for cleaning the nozzle 254. Moreover, the first pump is driven to flow the cleaning liquid into the nozzle 254 so that a turbulent flow is generated inside the nozzle 254 during cleaning. The nozzle 254 is cleaned upon every removal of the liquid component.

The BF separator 250 removes impurities and buffy coat component that interfere with the second measurement from the composite in which the test substance and the magnetic particles are connected with each other. The test substance in the second measurement unit 62 is, for example, an antigen, an antibody, a protein, or the like. In an embodiment, since the second sample is aspirated after aspiration of the first sample, a buffy coat is likely to be mixed into the second sample compared with the first sample. However, the BF separator 250 also removes the buffy coat mixed into the second sample together with the impurities. Thus, the second measurement for the immunological test can be properly performed.

Subsequently, the transfer section 310 takes the reaction container 22 subjected to the processing in the BF separator 250 out of the holding hole 252a and sets the reaction container 22 above the cleaning tank 205. In this state, the dispenser 320 uses the nozzle 326 to aspirate R3 reagent from the reagent container 233 set in the reagent aspirating position 223 and discharge the aspirated R3 reagent into the reaction container 22 set above the cleaning tank 205. Then, the transfer section 310 sets the reaction container 22 having R3 reagent discharged thereinto in the holding hole 241 of the heater 240. After the reaction container 22 is heated for a predetermined time by the heater 240, the transfer section 310 takes the reaction container 22 out of the holding hole 241 and transfers the reaction container 22 to the BF separator 250. Then, the BF separator 250 performs the BF separation processing again.

Here, R3 reagent contains a labeling antibody in which an antibody is used as a capturing substance. When R3 reagent is discharged into the reaction container 22 and the reaction container 22 is heated by the heater 240, a composite in which the test substance, the capturing antibody, the magnetic particles, and the labeling antibody are connected with each other is generated.

Then, the transfer section 310 takes the reaction container 22 processed twice by the BF separator 250 out of the holding hole 252a and sets the reaction container 22 immediately below a nozzle 261 of the reagent dispenser 260. The reagent dispenser 260 includes the nozzle 261 for discharging R4 reagent and a nozzle 262 for discharging R5 reagent. The reagent dispenser 260 also includes a mechanism to transfer the nozzles 261 and 262 in the Z-axis direction.

The reagent dispenser 260 uses the nozzle 261 to discharge R4 reagent into the reaction container 22. Thereafter, the transfer section 310 sets the reaction container 22 having R4 reagent discharged thereinto immediately below the nozzle 262. The reagent dispenser 260 uses the nozzle 262 to discharge R5 reagent into the reaction container 22. Note that R4 reagent and R5 reagent are housed in reagent containers 271 and 272 provided in the reagent housing section 270, respectively, and the nozzles 261 and 262 are connected to the reagent containers 271 and 272, respectively, through unillustrated flow paths.

Here, R4 reagent is a reagent for dispersing the composite in the reaction container 22. When the composite is mixed with R4 reagent, the composite is dispersed in the reaction container 22. R5 reagent is a reagent containing a luminescent substrate that emits light by reaction with the labeling antibody connected with the composite. When the composite is mixed with R5 reagent, the labeling antibody connected with the composite reacts with the luminescent substrate to generate chemiluminescence. Thus, a measurement specimen for use in the second measurement is prepared.

The transfer section 310 sets the reaction container 22 having R5 reagent discharged thereinto in the holding hole 241 of the heater 240. After the reaction container 22 is heated for a predetermined time by the heater 240, the transfer section 310 takes the reaction container 22 out of the holding hole 241 and sets the reaction container 22 in a holding hole 281a provided in the member 281.

The second measurement section 52 includes a lid 52a and a holding hole 52b. The lid 52a is configured to be openable and closable above the holding hole 52b. When the reaction container 22 is set in the holding hole 281a, the lid 52a is opened and the transfer section 282 takes the reaction container 22 out of the holding hole 281a and sets the reaction container 22 in the holding hole 52b of the second measurement section 52. Then, the lid 52a is closed and light generated from the measurement specimen in the reaction container 22 is measured in the holding hole 52b. Upon completion of the measurement of the measurement specimen in the reaction container 22, the reaction container 22 is disposed of through the disposal port 283 by the transfer section 282.

As illustrated in FIG. 12A, the first measurement section 51 that performs blood coagulation test-related measurement includes a light source section 411 and a light receiver 412, in addition to the holding hole 51a described above. FIG. 12A illustrates the vicinity of one holding hole 51a.

The light source section 411 includes a semiconductor laser light source and emits light having different wavelengths. The light source section 411 irradiates the reaction container 21 set in each holding hole 51a with light. When the measurement specimen in the reaction container 21 is irradiated with light, light transmitted through the measurement specimen or light scattered by the measurement specimen enters the light receiver 412. The light receiver 412 is provided for each holding hole 51a and includes a photodetector. To be more specific, the light receiver 412 includes a photoelectric tube, a photodiode, or the like. The light receiver 412 receives transmitted light or scattered light and outputs an electric signal corresponding to an amount of light received. Based on the electric signal outputted from the light receiver 412, the controller 61a generates measurement data for use in blood coagulation test-related analysis.

As illustrated in FIG. 12B, the second measurement section 52 that performs immunological test-related measurement includes a light receiver 421 in addition to the holding hole 52b described above. FIG. 12B illustrates the vicinity of the holding hole 52b.

The chemiluminescence generated from the measurement specimen housed in the reaction container 22 enters the light receiver 421. The light receiver 421 includes a photodetector capable of photon counting. To be more specific, the light receiver 421 includes a photomultiplier tube. When the light receiver 421 includes a photomultiplier tube capable of photon counting, the second measurement section 52 can perform highly sensitive and highly accurate measurement. The light receiver 421 receives the chemiluminescence and outputs a pulse waveform corresponding to photons received. The second measurement section 52 uses its internal circuit to count photons at regular intervals based on an output signal from the light receiver 421 and output a count value. Based on the count value outputted from the second measurement section 52, the controller 62a generates measurement data for use in immunological test-related analysis.

Note that, as described above, the second measurement unit 62 may perform biochemical test-related measurement. In this case, the second measurement section 52 performs biochemical test-related measurement and has the same configuration as that for performing blood coagulation test-related measurement. More specifically, in the second measurement section 52 in this case, the light source section 411 irradiates the measurement specimen with light and the light receiver 412 receives transmitted light or scattered light generated from the measurement specimen. Then, based on an electric signal outputted from the light receiver 412, the controller 62a generates measurement data for use in biochemical test-related analysis.

Figure 13:
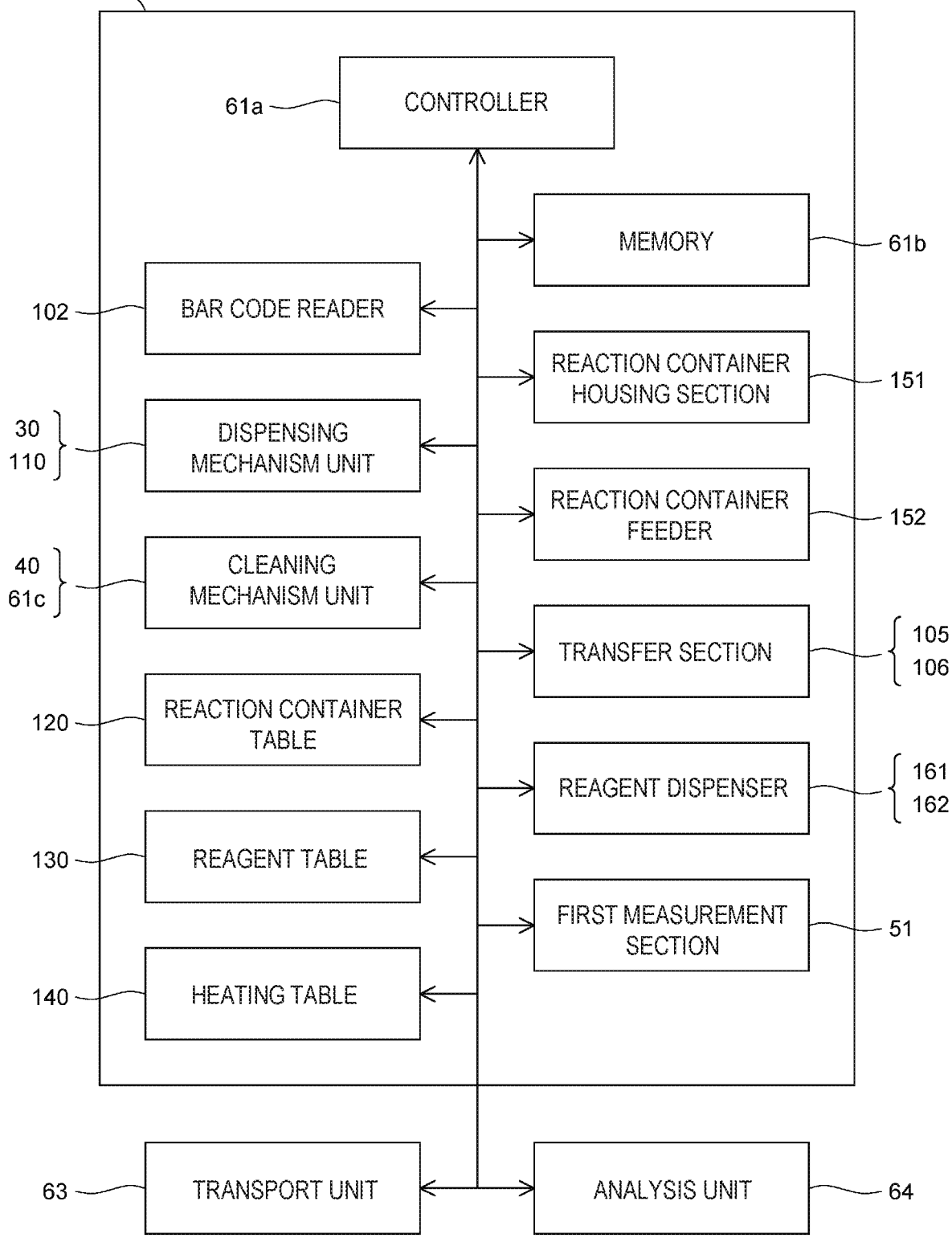
FIG. 13 is a diagram illustrating a view of a circuit configuration of a first measurement unit according to an embodiment.

As illustrated in FIG. 13, the first measurement unit 61 includes, as a configuration of a circuit section, the controller 61a, the bar code reader 102, the dispensing mechanism units 30 and 110, the cleaning mechanism unit 40, the reaction container table 120, the reagent table 130, the heating table 140, the reaction container housing section 151, the reaction container feeder 152, the transfer sections 105 and 106, the reagent dispensers 161 and 162, and the first measurement section 51, as described with reference to FIGS. 3 and 4. The dispensing mechanism unit 30 includes the sensor 35, the cleaner 36, and the drive sections 37 and 38 illustrated in FIG. 6.

As the configuration of the circuit section, the first measurement unit 61 also includes the memory 61b and a cleaning mechanism unit 61c. The controller 61a controls all the parts in the first measurement unit 61 and the transport unit 63 according to a program stored in the memory 61b. The memory 61b includes a ROM, a RAM, a hard disk, or the like. The cleaning mechanism unit 61c includes a cleaning tank 104 and flow paths and mechanism to flow a cleaning liquid into the cleaning tank 104 and the nozzle 111.

Figure 14:
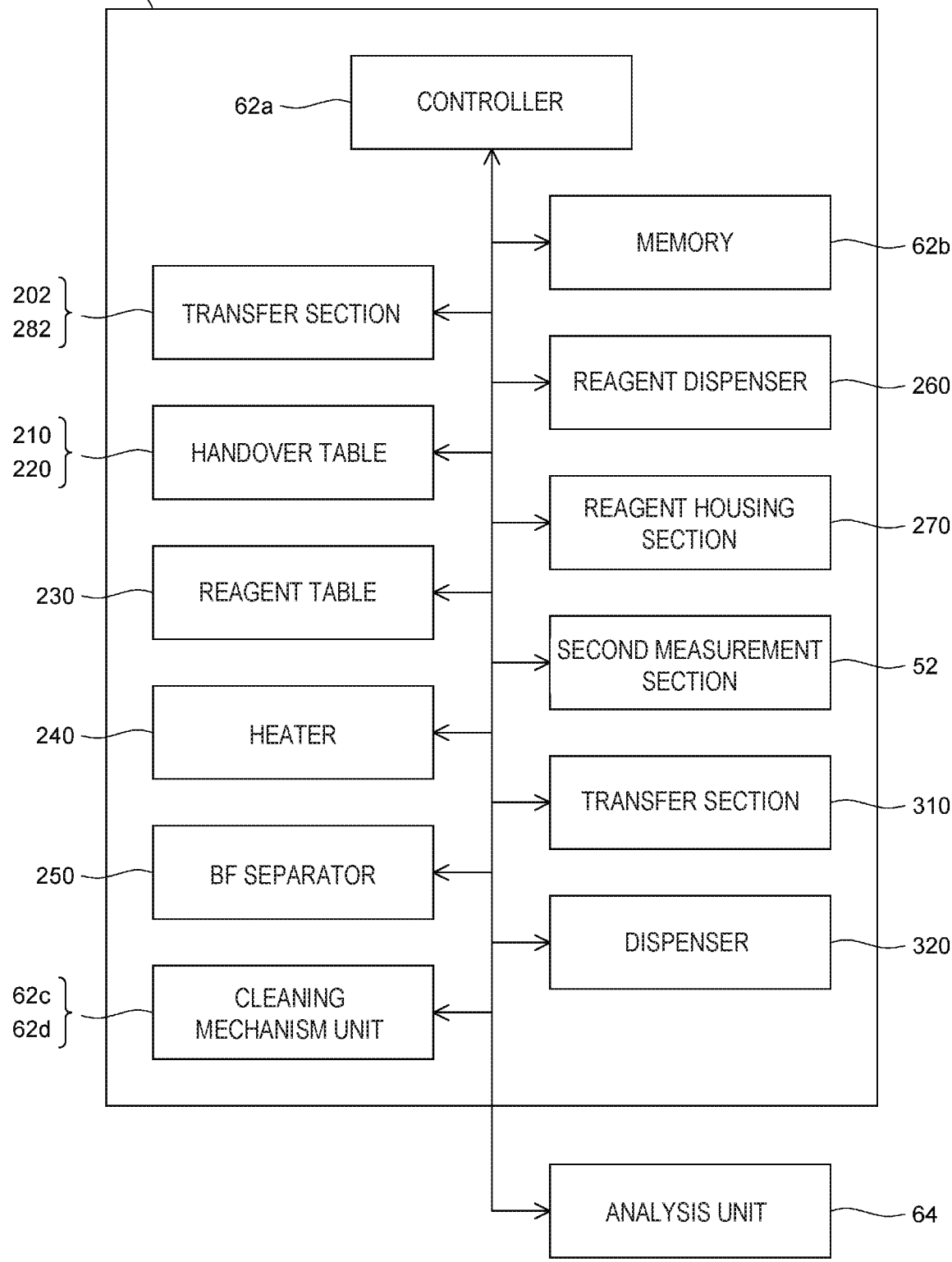
FIG. 14 is a diagram illustrating a view of a circuit configuration of a second measurement unit according to an embodiment.

As illustrated in FIG. 14, the second measurement unit 62 includes, as a configuration of a circuit section, the controller 62a, the transfer sections 202 and 282, the handover tables 210 and 220, the reagent table 230, the heater 240, the BF separator 250, the reagent dispenser 260, the reagent housing section 270, the second measurement section 52, the transfer section 310, and the dispenser 320, as described with reference to FIGS. 3, 10, and 11.

As the configuration of the circuit section, the second measurement unit 62 also includes the memory 62b and cleaning mechanism units 62c and 62d. The controller 62a controls all the parts in the second measurement unit 62 according to a program stored in the memory 62b. The memory 62b includes a ROM, a RAM, a hard disk, or the like. The cleaning mechanism unit 62c includes a cleaning tank 205 and flow paths and mechanism to flow a cleaning liquid into the cleaning tank 205 and the nozzles 325 and 326. The cleaning mechanism unit 62d includes a cleaning tank for cleaning the nozzle 254 in the BF separator 250 and flow paths and mechanism to flow a cleaning liquid into the cleaning tank and the nozzle 254.

Figure 15:
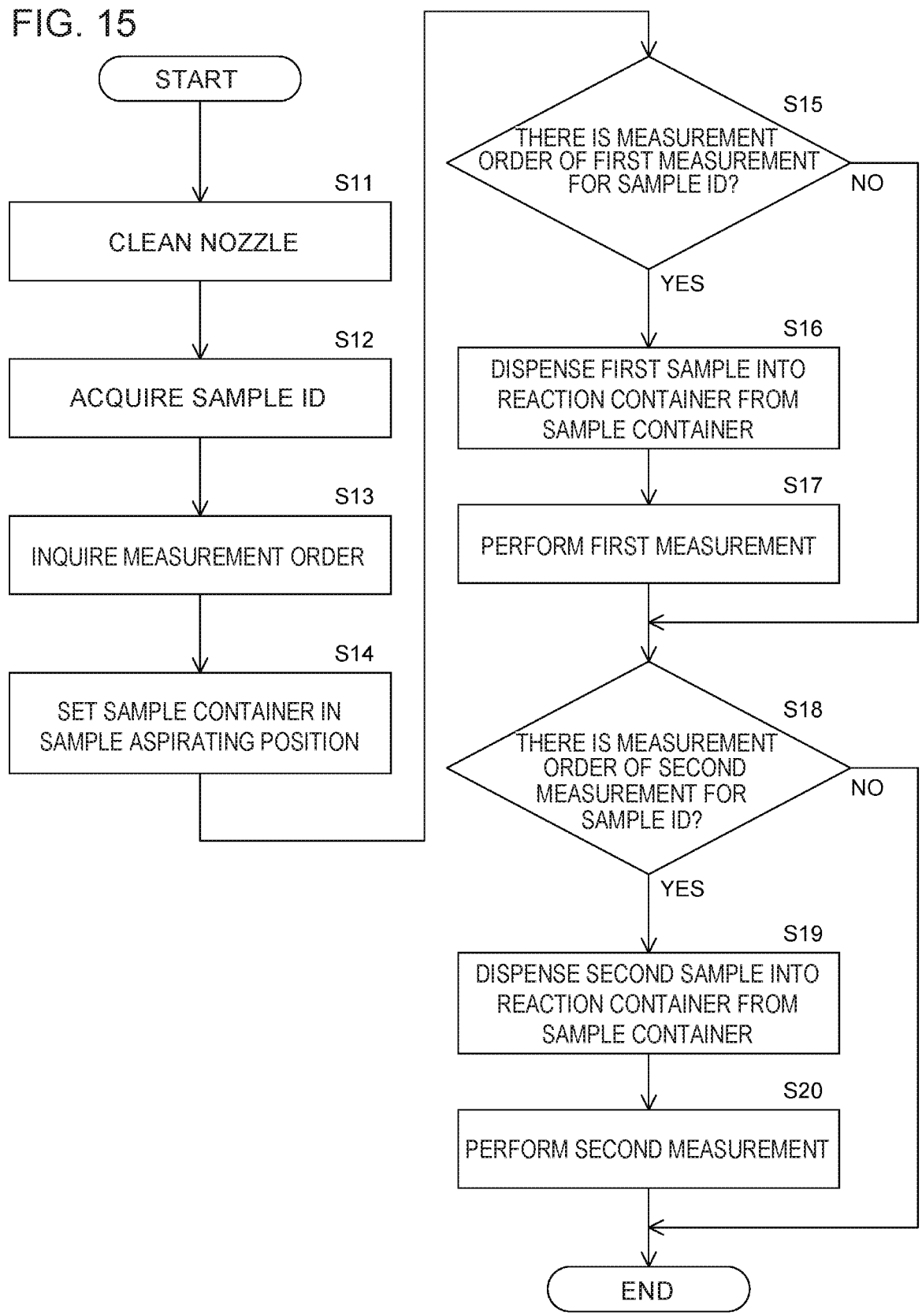
FIG. 15 is a flowchart illustrating processing of a sample measurement device according to an embodiment.

With reference to a flowchart illustrated in FIG. 15, processing of the sample measurement device 100 is described.

As illustrated in FIG. 15, when the sample measurement device 100 is started, the controller 61a drives the dispensing mechanism unit 30 and the cleaning mechanism unit 40 to clean the nozzle 31 of the dispensing mechanism unit 30 in Step S11. In Step S12, the controller 61a drives the transport unit 63 to transport the sample container 10 to in front of the bar code reader 102, and drives the bar code reader 102 to acquire the sample ID from the bar code label 14 on the sample container 10. In Step S13, the controller 61a makes an inquiry to the analysis unit 64 about a measurement order based on the sample ID acquired in Step S12, and acquires the inquiry result. In Step S14, the controller 61a drives the transport unit 63 to set the sample container 10 in the sample aspirating position 103a.

In Step S15, the controller 61a determines, based on the inquiry result of the measurement order, whether or not a blood coagulation test-related measurement order is set for the sample ID associated with the sample container 10 in the sample aspirating position 103a. When the blood coagulation test-related measurement order is set, the controller 61a drives the dispensing mechanism unit 30 in Step S16 to aspirate the sample in the sample container 10 and discharge the aspirated sample into a new reaction container 21 held by the reaction container table 120. The sample dispensed in Step S16 is a sample used for blood coagulation test-related measurement, which is the first sample as described above. Then, in Step S17, the controller 61a causes the first measurement section 51 to perform first measurement based on the first sample. On the other hand, when the blood coagulation test-related measurement order is not set, the processing in Steps S16 and S17 is skipped.

In Step S18, the controller 61a determines, based on the inquiry result of the measurement order, whether or not an immunological test-related measurement order is set for the sample ID associated with the sample container 10 in the sample aspirating position 103a. When the immunological test-related measurement order is set, the controller 61a drives the dispensing mechanism unit 30 in Step S19 to aspirate the sample in the sample container 10 and discharge the aspirated sample into a new reaction container 21 held by the reaction container table 120. The sample dispensed in Step S19 is a sample used for immunological test-related measurement, which is the second sample as described above. Then, in Step S20, the controller 61a causes the second measurement section 52 to perform second measurement based on the second sample. On the other hand, when the immunological test-related measurement order is not set, the processing in Steps S19 and S20 is skipped.

To aspirate the sample in Steps S16 and S19, the controller 61a drives the drive section 37 to lower the nozzle 31 to penetrate through the plug body 11 and then further lower the nozzle 31. Thereafter, after sensing through the sensor 35 that the tip 31a of the nozzle 31 comes into contact with the liquid surface of the plasma region, the controller 61a drives the drive section 37 according to the number of pulses stored in the memory 61b to lower the tip 31a of the nozzle 31 by a predetermined amount from the liquid surface of the plasma region. Thus, the tip 31a is set in a position lower than the liquid surface by the predetermined amount. In this state, the controller 61a drives the dispensing mechanism unit 30 to aspirate the sample. Then, after the aspiration of the sample, the controller 61a drives the dispensing mechanism unit 30 to take the nozzle 31 holding the aspirated sample out of the sample container 10 by lifting the nozzle 31 and discharge the aspirated sample into the reaction container 21.

Upon completion of the processing on one sample container 10 set in the sample aspirating position 103a as described above, the processing is returned to Step S11. Then, the controller 61a cleans the nozzle 31 of the dispensing mechanism unit 30 in Step S11. Thereafter, the controller 61a performs the processing in Steps S12 to S20 on the subsequent sample container 10.

<Another Configuration of Sample Measurement Device>

In the sample measurement device 100 illustrated in FIG. 3, one dispensing mechanism unit 30 dispenses the first and second samples from the sample container 10 transported by the transport unit 63. On the other hand, in the sample measurement device 100, the sample container 10 may be sequentially transported to the first measurement unit 61 and the second measurement unit 62, the dispensing mechanism unit 30 in the first measurement unit 61 may dispense the first sample, and the dispensing mechanism unit 430 in the second measurement unit 62 may dispense the second sample, as illustrated in FIG. 16.

Figure 16:
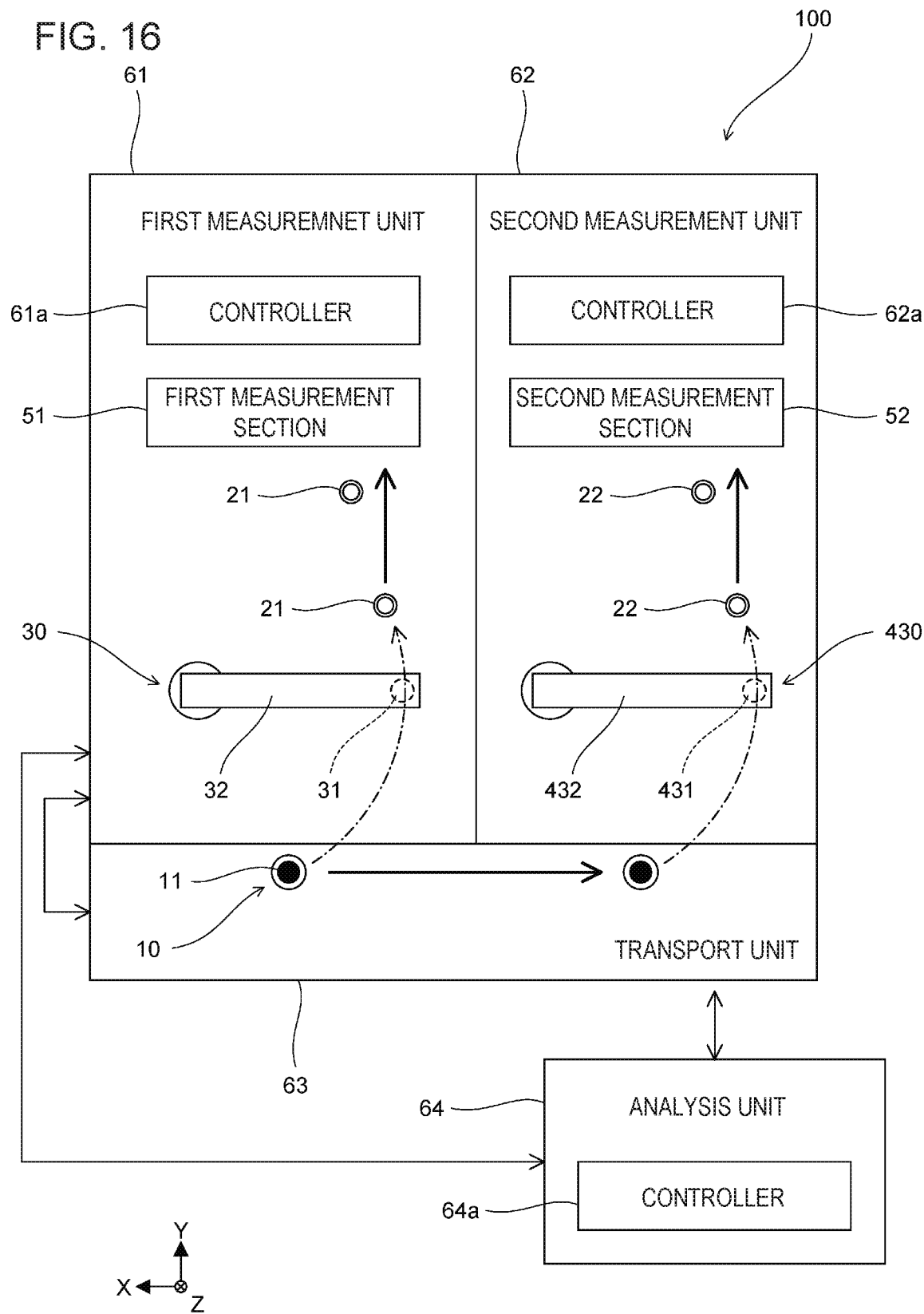
FIG. 16 is a diagram schematically illustrating a view of another configuration of a sample measurement device according to an embodiment.
Figure 17:
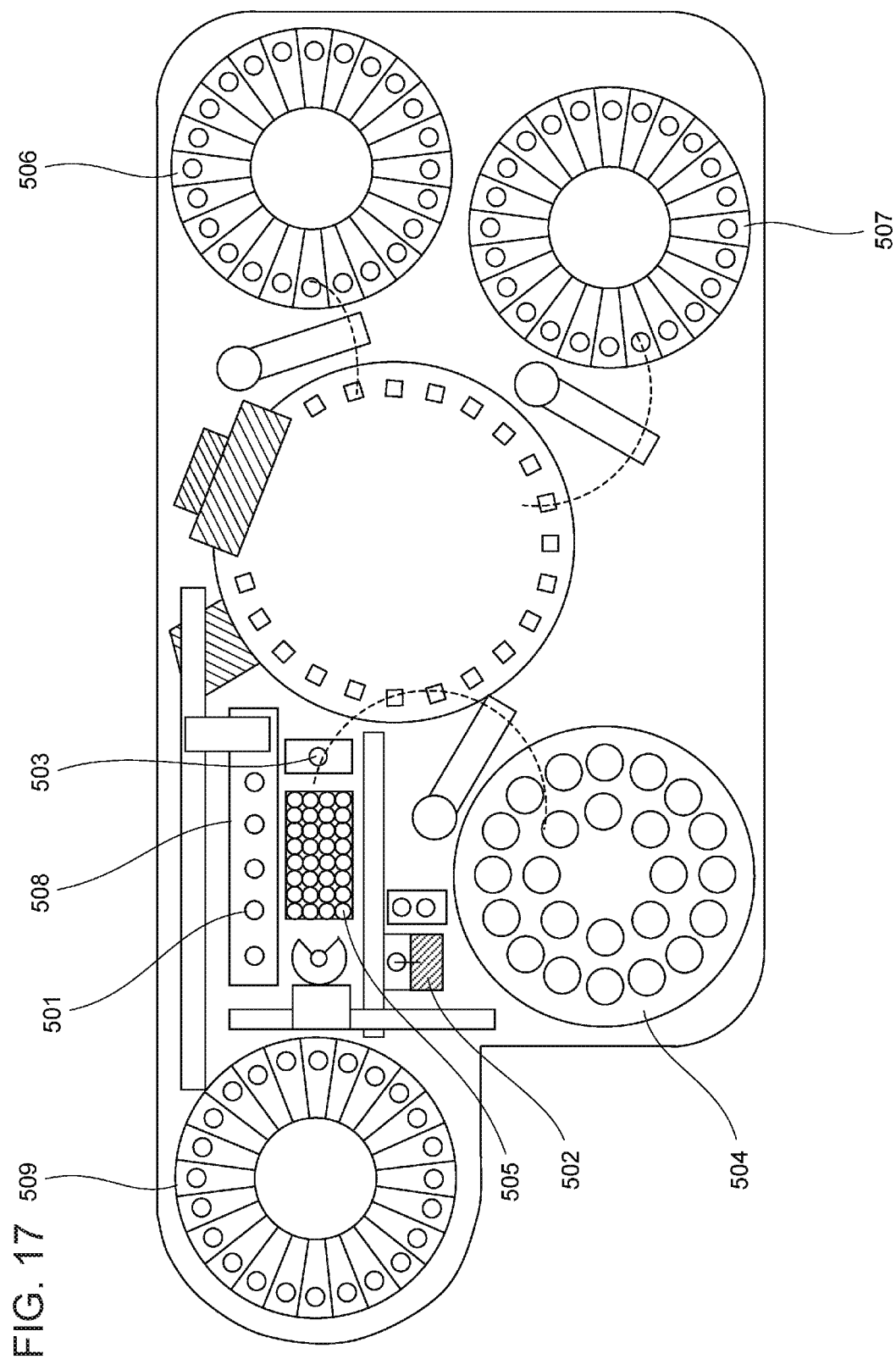
FIG. 17 is a diagram illustrating a schematic view of a configuration according to a related art.

In the configuration illustrated in FIG. 16, the dispensing mechanism unit 430 has the same configuration as that of the dispensing mechanism unit 30, and includes a nozzle 431 and an arm 432. In this case, as illustrated in the flowchart of FIG. 15, the first sample used for the first measurement is dispensed first into the reaction container 21 from the sample container 10, and then the second sample used for the second measurement is dispensed next into the reaction container 22 from the sample container 10. Thereafter, the nozzle 31 is cleaned every time the first sample is dispensed, and the nozzle 431 is cleaned every time the second sample is dispensed. The dispensing mechanism unit 430 is controlled by the controller 62a, and the number of pulses for lowering the nozzle 431 from the liquid surface by a predetermined amount is stored in the memory 62b.

According to the configuration of FIG. 16, as in the case of the sample measurement device 100 illustrated in FIG. 3, mixing of the buffy coat into the first sample is suppressed. Thus, the first measurement can be properly performed. Moreover, the nozzles 31 and 431 are cleaned upon every dispensing of the samples. Thus, carry-over due to accidental mixing of another sample into the first and second samples can be suppressed.

The invention includes other embodiments in addition to the above-described embodiments without departing from the spirit of the invention. The embodiments are to be considered in all respects as illustrative, and not restrictive. The scope of the invention is indicated by the appended claims rather than by the foregoing description. Hence, all configurations including the meaning and range within equivalent arrangements of the claims are intended to be embraced in the invention.

The invention claimed is:

1. A sample measurement device comprising:
a first measurement section configured to perform a first measurement for a blood coagulation test;
a second measurement section configured to perform a second measurement for a test different from the blood coagulation test;
a dispensing mechanism unit configured to dispense plasma from a sample container, which contains plasma, a buffy coat, and red blood cells, using a nozzle, the dispensing mechanism unit including the nozzle configured to aspirate and discharge the plasma and a drive section for lifting and lowering the nozzle, the sample measurement device; and
a controller configured to:
cause the dispensing mechanism unit to lower the nozzle to aspirate the plasma for use in the first measurement from the sample container by lowering the nozzle to a first position in the sample container;
lift the nozzle holding the aspirated plasma, discharge the plasma from the sample container into a first container for use in the blood coagulation test;
cause the dispensing mechanism unit to lower the nozzle to aspirate the plasma for use in the second measurement from the sample container by lowering the nozzle to a second position lower than the first position in the same sample container;
dispense the plasma for use in the second measurement from the sample container into a second container different from the first container, and
wherein dispensing comprises the lowering of the nozzle to aspirate the plasma for use in the first measurement from the sample container by the lowered nozzle, lifting the nozzle holding the aspirated plasma, and discharging the plasma into the first container, before dispensing plasma for use in the second measurement.

2. The sample measurement device according to claim 1, further comprising
a memory that stores a lowering amount of the nozzle, wherein
the controller drives the drive section according to the lowering amount stored in the memory to lower the nozzle by a predetermined amount from a liquid surface of the sample.

3. The sample measurement device according to claim 2, wherein
the drive section is a stepping motor,
the memory stores the number of pulses corresponding to the lowering amount, and
the controller drives the drive section according to the number of pulses stored in the memory to lower the nozzle by the predetermined amount from the liquid surface of the sample.

4. The sample measurement device according to claim 1, further comprising
a sensor that senses that a tip of the nozzle comes into contact with a liquid surface, wherein
the controller controls the dispensing mechanism unit to lower, after the sensor senses that the tip of the nozzle comes into contact with a liquid surface of the sample, the nozzle by a predetermined amount from the liquid surface of the sample.

5. A sample measurement method of performing first measurement for a blood coagulation test and second measurement for a test different from the blood coagulation test, comprising:

providing a dispensing mechanism unit including a nozzle for dispensing plasma from a sample container, which contains plasma separated from whole blood by centrifugation, wherein a buffy coat is formed between a plasma region and a red blood cell region in the sample container;

dispensing, from the sample container, plasma for use in the first measurement into a first container;

dispensing, from the sample container, plasma for use in the second measurement into a second container different from the first container;

performing the first measurement based on the plasma dispensed into the first container; and performing the second measurement based on the plasma dispensed into the second container;

wherein dispensing plasma for use in the first measurement for the blood coagulation test is performed through a nozzle positioned at a first position in the sample container and before dispensing plasma for use in the second measurement for the test different from the blood coagulation test, and wherein dispensing plasma for use in the first measurement comprises a first aspiration operation and dispensing plasma for use in the second measurement comprises a second aspiration operation through the nozzle at a second position lower than the first position.

6. The sample measurement method according to claim 5, further comprising centrifuging whole blood in the sample container to separate the plasma region from the red blood cell region with the buffy coat therebetween.

7. The sample measurement method according to claim 5, wherein aspirating the sample from the sample container through the nozzle in the first dispense operation comprises aspirating the sample from the sample container through the nozzle with a tip of the nozzle positioned above a central position of the plasma region in the sample container.

8. The sample measurement method according to claim 5, wherein performing the first dispense operation comprises lowering the nozzle by a predetermined amount from a liquid surface of the plasma region in the sample container and aspirating the sample from the sample container by using the lowered nozzle, and performing the second dispense operation comprises lowering the nozzle by a predetermined amount from the liquid surface of the plasma region in the sample container and aspirating the sample from the sample container by using the lowered nozzle.

9. The sample measurement method according to claim 8, wherein the lowering of the nozzle by the predetermined amount from the liquid surface of the plasma region in the sample container in one of the first dispense operation and the second dispense operation comprises lowering the nozzle by the predetermined amount from the liquid surface of the plasma region in the sample container by driving a drive section that lifts and lowers the nozzle according to a lowering amount stored in a memory.

10. The sample measurement method according to claim 8, wherein the lowering of the nozzle by the predetermined amount from the liquid surface of the plasma region in the sample container in one of the first dispense operation and the second dispense operation comprises lowering the nozzle by the predetermined amount from the liquid surface of the plasma region in the sample container after a sensor senses that a tip of the nozzle comes into contact with the liquid surface of the plasma region.

11. The sample measurement method according to claim 5, wherein the nozzle comprises a first nozzle used for the first dispense operation and a second nozzle used for the second dispense operation.

12. The sample measurement method according to claim 5, wherein the same nozzle is used to dispense the sample for use in the first measurement and to dispense the sample for use in the second measurement.

13. The sample measurement method according to claim 5, further comprising cleaning, with a cleaning liquid, inner and outer peripheral surfaces of at least a part of the nozzle with which the sample has come into contact.

14. The sample measurement method according to claim 5, wherein the sample container is a blood collection tube.

15. The sample measurement method according to claim 5, wherein the second measurement is measurement for an immunological test.

16. The sample measurement method according to claim 15, further comprising performing BF separation to separate a liquid component from a test substance in the sample dispensed into the second container.

17. The sample measurement method according to claim 5, wherein the second measurement is measurement for a biochemical test.

* * * * *